United States Patent
Hovda et al.

[11] Patent Number: 6,063,079
[45] Date of Patent: May 16, 2000

[54] METHODS FOR ELECTROSURGICAL TREATMENT OF TURBINATES

[75] Inventors: David C. Hovda, Mountain View; Hira V. Thapliyal, Los Altos, both of Calif.; Philip E. Eggers, Dublin, Ohio; Maria B. Ellsberry, Fremont, Calif.

[73] Assignee: ArthroCare Corporation, Sunnyvale, Calif.

[21] Appl. No.: 09/054,323

[22] Filed: Apr. 2, 1998

Related U.S. Application Data

[63] Continuation-in-part of application No. 08/990,374, Dec. 15, 1997, which is a continuation-in-part of application No. 08/485,219, Jun. 7, 1995, Pat. No. 5,697,281.

[51] Int. Cl.[7] ................................... A61B 18/14
[52] U.S. Cl. .................. 606/41; 606/45; 606/46; 606/48; 606/49; 606/50; 607/DIG. 99; 607/105; 607/113; 604/114; 128/898
[58] Field of Search ............................. 606/32, 41, 45, 606/46, 48, 49, 50; 607/99, 105, 113, 122; 604/22, 114; 128/898

[56] References Cited

U.S. PATENT DOCUMENTS

| | | | |
|---|---|---|---|
| 2,050,904 | 8/1996 | Trice | 128/303 |
| 4,033,351 | 7/1977 | Hetzel | 128/303 |

(List continued on next page.)

FOREIGN PATENT DOCUMENTS

| | | | |
|---|---|---|---|
| 0703461 | 3/1996 | European Pat. Off. | G01R 27/02 |
| 0740926 | 11/1996 | European Pat. Off. | A61B 17/39 |
| 0754437 | 1/1997 | European Pat. Off. | A61B 17/39 |
| 57-117843 | 7/1982 | Japan | A61B 17/39 |
| 2308979 | 7/1997 | United Kingdom | A61B 17/39 |
| 2308980 | 7/1997 | United Kingdom | A61B 17/36 |
| 2308981 | 7/1997 | United Kingdom | A61B 17/39 |
| 2327350 | 1/1999 | United Kingdom | A61B 17/39 |

(List continued on next page.)

OTHER PUBLICATIONS

C. Slager et al. (1987) Z. Kardiologie 76 (6):67–71.
C. Slager et al. (1985) JACC 5 (6):1382–6.
P. Nardella (1989) SPIE 1068:42–49.
Elsasser et al. (1976) Medizinal–Markt/Acta Medicotechnica 24 (4):129–134.
E. Kramolowsky et al. (1991) J. of Urology 146:669–674.
R. Tucker et al. (1990) Urol. Res. 18:291–294.
R. Tucker et al. (1989) J. of Urology 141:662–665.
R. Tucker et al. (1989) Abstract P14–11, 7th World Congress on Endourology and ESWL, Nov. 27–30, 1989, Kyoto, Japan.
Rand et al. (1985) J. Arthro. Surg. 1:242–246.
J. Pearce Electrosurgery, John Wiley & Sons, New York, 1986.

Primary Examiner—Lee Cohen
Attorney, Agent, or Firm—John T. Raffle

[57] ABSTRACT

The present invention provides systems and methods for selectively applying electrical energy to a target location within the head and neck of a patient's body, particularly including tissue in the ear, nose and throat. In one aspect, a method is provided for reducing the volume of enlarge swollen tissue in the patient's nose, such as swollen nasal tissue, mucus membranes, turbinates, polyps, neoplasms, cartilage (e.g., the nasal septum) or the like. In particular, the turbinates are treated by positioning one or more electrode terminal(s) adjacent to the turbinates, and delivering electrically conductive fluid, such as isotonic saline, to the nasal cavity to substantially surround the electrode terminal(s) with the fluid. High frequency voltage is applied between the electrode terminal(s) and one or more return electrode(s) to remove a small tissue segment, channel or hole from the region near or in the turbinates to shrink the turbinates and prevent swelling, due to the formation of scar tissue as the wound heals. The high frequency voltage may be selected to effect a small amount of thermal damage to the walls of the channel or hole to facilitate the formation of scar tissue without extending this thermal damage beyond the immediate region of the target site.

18 Claims, 18 Drawing Sheets

U.S. PATENT DOCUMENTS

| | | | |
|---|---|---|---|
| 4,040,426 | 8/1977 | Morrison, Jr. | 128/303 |
| 4,043,342 | 8/1977 | Morrison, Jr. | 128/303 |
| 4,116,198 | 9/1978 | Roos | 128/303 |
| 4,202,337 | 5/1980 | Hren et al. | 128/303 |
| 4,228,800 | 10/1980 | Degler, Jr. et al. | 128/303 |
| 4,232,676 | 11/1980 | Herczog | 128/303 |
| 4,248,231 | 2/1981 | Herczog et al. | 128/303 |
| 4,326,529 | 4/1982 | Doss et al. | 128/303 |
| 4,381,007 | 4/1983 | Doss | 128/303 |
| 4,476,862 | 10/1984 | Pao | 128/303 |
| 4,532,924 | 8/1985 | Auth et al. | 128/303 |
| 4,548,207 | 10/1985 | Reimels | 128/303 |
| 4,567,890 | 2/1986 | Ohta et al. | 128/303 |
| 4,593,691 | 6/1986 | Lindstrom et al. | 128/303.14 |
| 4,674,499 | 6/1987 | Pao | 128/303 |
| 4,682,596 | 7/1987 | Bales et al. | 604/22 |
| 4,706,667 | 11/1987 | Roos | 128/303 |
| 4,765,331 | 8/1988 | Petruzzi et al. | 128/303 |
| 4,823,791 | 4/1989 | D'Amelio | 128/303 |
| 4,860,752 | 8/1989 | Turner | 128/422 |
| 4,931,047 | 6/1990 | Broadwin et al. | 604/22 |
| 4,936,301 | 6/1990 | Rexroth et al. | 606/45 |
| 4,943,290 | 7/1990 | Rexroth et al. | 606/45 |
| 4,967,765 | 11/1990 | Turner et al. | 128/785 |
| 4,976,711 | 12/1990 | Parins et al. | 606/48 |
| 4,979,948 | 12/1990 | Geddes et al. | 606/33 |
| 4,998,933 | 3/1991 | Eggers et al. | 606/41 |
| 5,007,908 | 4/1991 | Rydell | 606/47 |
| 5,009,656 | 4/1991 | Reimels | 128/303 |
| 5,035,696 | 7/1991 | Rydell | 606/47 |
| 5,057,105 | 10/1991 | Malone et al. | 606/28 |
| 5,057,106 | 10/1991 | Kasevich et al. | 606/33 |
| 5,078,717 | 1/1992 | Parins et al. | 606/48 |
| 5,080,660 | 1/1992 | Buelna | 606/48 |
| 5,083,565 | 1/1992 | Parins | 128/642 |
| 5,098,431 | 3/1992 | Rydell | 606/48 |
| 5,108,391 | 4/1992 | Flachenecker et al. | 606/38 |
| 5,112,330 | 5/1992 | Nishigaki et al. | 606/46 |
| 5,122,138 | 6/1992 | Manwaring | 606/46 |
| 5,125,928 | 6/1992 | Parins et al. | 606/48 |
| 5,178,620 | 1/1993 | Eggers et al. | 606/41 |
| 5,190,517 | 3/1993 | Zieve et al. | 604/22 |
| 5,195,959 | 3/1993 | Smith | 604/34 |
| 5,196,007 | 3/1993 | Ellman et al. | 606/32 |
| 5,197,963 | 3/1993 | Parins | 606/46 |
| 5,217,457 | 6/1993 | Delahuerga et al. | 606/42 |
| 5,249,585 | 10/1993 | Turner | 607/99 |
| 5,267,994 | 12/1993 | Gentelia et al. | 606/15 |
| 5,267,997 | 12/1993 | Farin et al. | 606/38 |
| 5,273,524 | 12/1993 | Fox et al. | 604/21 |
| 5,277,201 | 1/1994 | Stern | 607/98 |
| 5,281,216 | 1/1994 | Klicek | 606/42 |
| 5,281,218 | 1/1994 | Imran | 606/41 |
| 5,290,282 | 3/1994 | Casscells | 606/29 |
| 5,300,069 | 4/1994 | Hunsberger et al. | 606/37 |
| 5,312,400 | 5/1994 | Bales et al. | 606/41 |
| 5,314,406 | 5/1994 | Arias et al. | 604/21 |
| 5,324,254 | 6/1994 | Phillips | 604/21 |
| 5,330,470 | 7/1994 | Hagen | 606/42 |
| 5,334,140 | 8/1994 | Phillips | 604/35 |
| 5,334,183 | 8/1994 | Wuchinich | 606/46 |
| 5,336,220 | 8/1994 | Ryan et al. | 604/22 |
| 5,336,443 | 11/1994 | Eggers et al. | 604/114 |
| 5,342,357 | 8/1994 | Nardella | 606/40 |
| 5,370,675 | 12/1994 | Edwards et al. | 607/101 |
| 5,380,277 | 1/1995 | Phillps | 604/33 |
| 5,383,876 | 1/1995 | Nardella | 606/49 |
| 5,383,917 | 1/1995 | Desai et al. | 607/702 |
| 5,395,312 | 3/1995 | Desai | 604/22 |
| 5,395,368 | 3/1995 | Ellman et al. | 606/45 |
| 5,417,687 | 5/1995 | Nardella et al. | 606/32 |
| 5,419,767 | 5/1995 | Eggers et al. | 604/114 |
| 5,423,812 | 6/1995 | Ellman et al. | 606/45 |
| 5,441,499 | 8/1995 | Fritzsch | 606/45 |
| 5,454,809 | 10/1995 | Janssen | 606/41 |
| 5,456,662 | 10/1995 | Edwards et al. | 604/22 |
| 5,490,850 | 2/1996 | Ellman . | |
| 5,505,728 | 4/1996 | Ellman et al. | 606/39 |
| 5,514,130 | 5/1996 | Baker | 606/41 |
| 5,556,397 | 9/1996 | Long et al. | 606/48 |
| 5,562,503 | 10/1996 | Ellman et al. | 439/638 |
| 5,562,703 | 10/1996 | Desai | 606/210 |
| 5,569,242 | 10/1996 | Lax et al. | 606/42 |
| 5,571,101 | 11/1996 | Ellman et al. | 606/45 |
| 5,584,872 | 12/1996 | LaFontaine et al. | 607/116 |
| 5,609,151 | 3/1997 | Mulier et al. | 128/642 |
| 5,624,439 | 4/1997 | Edwards et al. | 606/45 |
| 5,630,812 | 5/1997 | Ellman et al. | 606/41 |
| 5,647,869 | 7/1997 | Goble | 606/37 |
| 5,662,680 | 9/1997 | Desai | 606/210 |
| 5,674,191 | 10/1997 | Edwards et al. | 604/22 |
| 5,676,693 | 10/1997 | LaFontaine | 607/116 |
| 5,681,282 | 10/1997 | Eggers et al. | 604/114 |
| 5,683,366 | 11/1997 | Eggers et al. | 604/114 |
| 5,683,386 | 11/1997 | Ellman et al. | 606/41 |
| 5,683,387 | 11/1997 | Garito | 606/45 |
| 5,695,495 | 12/1997 | Ellman et al. | 606/41 |
| 5,697,281 | 12/1997 | Eggers et al. | 604/114 |
| 5,697,536 | 12/1997 | Eggers et al. | 604/114 |
| 5,697,882 | 12/1997 | Eggers et al. | 604/114 |
| 5,697,909 | 12/1997 | Eggers et al. | 604/114 |
| 5,700,262 | 12/1997 | Acosta | 606/48 |
| 5,707,349 | 1/1998 | Edwards | 604/22 |
| 5,718,702 | 2/1998 | Edwards | 606/41 |
| 5,725,524 | 3/1998 | Mulier et al. | 606/41 |
| 5,733,282 | 3/1998 | Ellman et al. | 606/45 |
| 5,738,114 | 4/1998 | Edwards | 128/889 |
| 5,746,224 | 5/1998 | Edwards | 606/41 |
| 5,749,869 | 5/1998 | Lindenmeier | 606/34 |
| 5,766,153 | 6/1998 | Eggers et al. | 604/114 |
| 5,775,338 | 7/1998 | Hastings | 128/898 |
| 5,800,379 | 9/1998 | Edwards | 604/22 |
| 5,800,429 | 9/1998 | Edwards | 606/41 |
| 5,807,395 | 9/1998 | Mulier et al. | 606/41 |
| 5,810,764 | 9/1998 | Eggers et al. | 604/23 |
| 5,817,049 | 10/1998 | Edwards | 604/22 |
| 5,820,580 | 10/1998 | Edwards et al. | 604/22 |
| 5,823,197 | 10/1998 | Edwards | 128/898 |
| 5,827,277 | 10/1998 | Edwards | 606/41 |
| 5,843,077 | 12/1998 | Edwards | 606/41 |
| 5,885,277 | 3/1999 | Korth | 606/35 |
| 5,897,553 | 4/1999 | Mulier et al. | 606/41 |
| 5,921,983 | 7/1999 | Shannon, Jr. | 606/45 |
| 5,944,715 | 8/1999 | Goble et al. | 606/41 |

FOREIGN PATENT DOCUMENTS

| | | | |
|---|---|---|---|
| 2327351 | 1/1999 | United Kingdom | A61B 17/39 |
| 2327352 | 1/1999 | United Kingdom | A61B 17/39 |
| WO 90/07303 | 7/1990 | WIPO | A61B 17/39 |
| WO 92/21278 | 12/1992 | WIPO | A61B 5/04 |
| 93/20747 | 10/1993 | WIPO | A61B 5/00 |
| 94/04220 | 3/1994 | WIPO | A61N 1/06 |
| 94/08654 | 4/1994 | WIPO | A61M 37/00 |
| 96/00042 | 1/1996 | WIPO | A61B 17/39 |
| 97/00646 | 1/1997 | WIPO | A61B 17/39 |
| 97/00647 | 1/1997 | WIPO | A61B 17/39 |
| 97/24073 | 7/1997 | WIPO | A61B 17/39 |
| 97/24993 | 7/1997 | WIPO | A61B 17/39 |
| 97/24994 | 7/1997 | WIPO | A61B 17/39 |
| 97/30644 | 8/1997 | WIPO | A61B 17/39 |
| 97/30645 | 8/1997 | WIPO | A61B 17/39 |
| 97/30646 | 8/1997 | WIPO | A61B 17/39 |

| | | | | | | | | | |
|---|---|---|---|---|---|---|---|---|---|
| 97/30647 | 8/1997 | WIPO | ............................ | A61B 17/39 | 97/43972 | 11/1997 | WIPO | ............................ | A61B 17/39 |
| 97/41785 | 11/1997 | WIPO | ............................ | A61B 17/39 | 97/43973 | 11/1997 | WIPO | ............................ | A61B 17/39 |
| 97/41786 | 11/1997 | WIPO | ............................ | A61B 17/39 | 97/44092 | 11/1997 | WIPO | ............................ | A61N 1/40 |
| 97/41787 | 11/1997 | WIPO | ............................ | A61B 17/39 | 97/48346 | 12/1997 | WIPO | ............................ | A61B 17/39 |
| 97/41788 | 11/1997 | WIPO | ............................ | A61B 17/39 | WO 98/27879 | 7/1998 | WIPO | ............................ | A61B 17/36 |
| 97/43969 | 11/1997 | WIPO | ............................ | A61B 17/39 | 99/08613 | 2/1999 | WIPO | ............................ | A61B 17/36 |
| 97/43970 | 11/1997 | WIPO | ............................ | A61B 17/39 | | | | | |

METHODS FOR ELECTROSURGICAL TREATMENT OF TURBINATES

RELATED APPLICATIONS

The present invention is a continuation-in-part of U.S. patent application Ser. No. 08/990,374, filed Dec. 15, 1997, which is a continuation-in-part of U.S. patent application Ser. No. 08/485,219, filed on Jun. 7, 1995,now U.S. Pat. No. 5,697,281, the complete disclosures of which are incorporated herein by reference for all purposes.

The present invention is related to commonly assigned co-pending Provisional Patent Application No. 60/075,059, filed on Feb. 18, 1998, U.S. patent application Ser. No. 09/010,382, filed Jan. 21, 1998, and U.S. patent application entitled "Systems and Methods for Selective Electrosurgical Treatment of Body Structures", filed Feb. 27, 1998, U.S. patent application Ser. Nos. 08/977,845, filed on Nov. 25, 1997, 08/942,580, filed on Oct. 2, 1997, 09/026,851, filed Feb. 20, 1998, U.S. application Ser. No. 08/753,227, filed on Nov. 22, 1996 , now U.S. Pat. No. 5,873,855, U.S. application Ser. No. 08/687792, filed on Jul. 18, 1996 , now U.S. Pat. No. 5,843,019, and PCT International Application, U.S. National Phase Ser. No. PCT/US94/05168, filed on May 10, 1994, now U.S. Pat. No. 5,697,909, which was a continuation-in-part of U.S. patent application Ser. No. 08/059,681, filed on May 10, 1993 , now abandoned, which was a continuation-in-part of U.S. patent application Ser. No. 07/958,977, filed on Oct. 9, 1992, now U.S. Pat. No. 5,366,448,which was a continuation-in-part of U.S. patent application Ser. No. 07/817,575, filed on Jan. 7, 1992 now abandoned, the complete disclosures of which are incorporated herein by reference for all purposes. The present invention is also related to commonly assigned U.S. Pat. No. 5,683,366, filed Nov. 22, 1995, the complete disclosure of which is incorporated herein by reference for all purposes.

BACKGROUND OF THE INVENTION

The present invention relates generally to the field of electrosurgery, and more particularly to surgical devices and methods which employ high frequency electrical energy to treat tissue in regions of the head and neck, such as the ear, nose and throat. The present invention is particularly suited for treating enlarged nasal structures, such as turbinates, polyps or other sinus tissue.

Sinuses are the air-filled cavities insides the facial bones that open into the nasal cavities. Sinusitis is the inflammation of the mucous membranes of one or more of the paranasal sinus cavities. Sinusitis is often associated with a viral or bacterial upper respiratory infection that spreads to the sinuses. When the sinus opening becomes blocked, the cavities fill, producing deep pain and pressure. Postnasal or nasal drainage, nasal congestion with pressure, headaches, sinus infections and nasal polyps are most commonly associated with chronic sinusitis.

Treatment of mild sinusitis typically involves antibiotics, decongestants and analgesics, and is designed to prevent further complications. For more severe or chronic sinusitis, surgery is often necessary to return the nose and sinuses to normal function, particularly with patients who have undergone years of allergy treatment and still suffer from sinus blockage, or patients born with small sinuses and nasal passages. Recent developments in the field of endoscopic surgical techniques and medical devices have provided skilled physicians with instrumentation and methods to perform complicated paranasal sinus surgical procedures. Improved visualization of the nasal cavity and the paranasal sinuses, for example, has now made these anatomical areas more accessible to the endoscopic surgeon. As a result, functional endoscopic sinus surgery (FESS) has become the technique of choice in the surgical approach to sinus disease.

Another nasal symptom, runny noses (e.g., allergic rhinitis or vasomotor rhinitis), is typically caused by small shelf-like structures in the nose called turbinates. Turbinates are responsible for warming and humidifying the air passing through the nose into the lungs. When the air contains an irritant, the turbinates react to the airborne particles by swelling and pouring mucus, as if the body were trying to block and cleanse the breathing passage. Enlarged turbinates cause the air space through the nasal passages to become restricted. In these cases, it would be desirable to reduce the size of the turbinates to alleviate the constriction.

For temporary relief of swollen turbinates, pharmaceutical treatment, such as decongestant nasal sprays and pills, is often prescribed. These measures, however, have limited effectiveness, and the long term use of such nasal sprays typically makes the problem worse. Moreover, pharmaceuticals, particularly decongestant pills may cause high blood pressure, increase the heart rate and, for some people, cause sleeplessness.

Various surgical techniques exist to treat enlarged turbinates, with different instrumentation and degrees of invasiveness. Scalpels, electrocautery and powered instrumentation, such as microdebrider devices and lasers, have been used to reduce the size of body structures, such as swollen tissue, turbinates, polyps and the like. Microdebriders are disposable motorized cutters having a rotating shaft with a serrated distal tip for cutting and resecting tissue. The handle of the microdebrider is typically hollow, and it accommodates a small vacuum, which serves to aspirate debris. In this procedure, the distal tip of the shaft is endoscopically delivered through a nasal passage into the nasal cavity of a patient, and an endoscope is similarly delivered through the same or the opposite nasal passage to view the surgical site. An external motor rotates the shaft and the serrated tip, allowing the tip to cut the polyps or other swollen tissue responsible for the blockage. Once the critical blockage is cleared, aeration and drainage are reestablished and the sinuses heal and return to their normal function.

While microdebriders have been promising, these devices suffer from a number of disadvantages. For one thing, the tissue in the nasal and sinus cavities is extremely vascular, and the microdebrider severs blood vessels within this tissue, usually causing profuse bleeding that obstructs the surgeon's view of the target site. Controlling this bleeding can be difficult since the vacuuming action tends to promote hemorrhaging from blood vessels disrupted during the procedure. In addition, the microdebrider often must be removed from the nose periodically to cauterize severed blood vessels, which lengthens the procedure. Moreover, the serrated edges and other fine crevices of the microdebrider can easily become clogged with debris, which requires the surgeon to remove and clean the microdebrider during the surgery, further increasing the length of the procedure. More serious concerns, however, are that the microdebrider is not precise, and it is often difficult, during the procedure, to differentiate between the target sinus tissue, and other structures within the nose, such as cartilage, bone or cranial. Thus, the surgeon must be extremely careful to minimize damage to the cartilage and bone within the nose, and to avoid damaging nerves, such as the optic nerve.

Lasers were initially considered ideal for nasal surgery because lasers ablate or vaporize tissue with heat, which also acts to cauterize and seal the small blood vessels in the tissue. Unfortunately, lasers are both expensive and somewhat tedious to use in these procedures. Another disadvantage with lasers is the difficulty in judging the depth of tissue ablation. Since the surgeon generally points and shoots the laser without contacting the tissue, he or she does not receive any tactile feedback to judge how deeply the laser is cutting. Because healthy tissue, cartilage, bone and/or cranial nerves often lie within close proximity of the sinus tissue, it is essential to maintain a minimum depth of tissue damage, which cannot always be ensured with a laser.

Recently, RF energy has been used to treat body structures within the nose and throat, such as turbinates. This procedure, which was developed by Somnus Medical Technologies of Sunnyvale, Calif. involves the use of a monopolar electrode that directs RF current into the target tissue to desiccate or destroy portions of the tissue. Of course, such monopolar devices suffer from the disadvantage that the electric current will flow through undefined paths in the patient's body, thereby increasing the risk of unwanted electrical stimulation to portions of the patient's body. In addition, since the defined path through the patient's body has a relatively high impedance (because of the large distance or resistivity of the patient's body), large voltage differences must typically be applied between the return and active electrodes in order to generate a current suitable for ablation or cutting of the target tissue. This current, however, may inadvertently flow along body paths having less impedance than the defined electrical path, which will substantially increase the current flowing through these paths, possibly causing damage to or destroying surrounding tissue or neighboring nerves.

Another disadvantage of conventional RF devices, such as the Somnus monopolar electrode, is that these devices typically operate by creating a voltage difference between the active electrode and the target tissue, causing an electrical arc to form across the physical gap between the electrode and tissue. At the point of contact of the electric arcs with tissue, rapid tissue heating occurs due to high current density between the electrode and tissue. This high current density causes cellular fluids to rapidly vaporize into steam, thereby producing a "cutting effect" along the pathway of localized tissue heating. Thus, the tissue is parted along the pathway of evaporated cellular fluid, inducing undesirable collateral tissue damage in regions surrounding the target tissue site. This collateral tissue damage often causes indiscriminate destruction of turbinate tissue, resulting in the loss of the proper function of the turbinate.

SUMMARY OF THE INVENTION

The present invention provides systems, apparatus and methods for selectively applying electrical energy to structures in the head and neck of a patient's body, such as tissue within the ear, nose and throat. The systems and methods of the present invention are particularly useful for ablation and hemostasis of swollen or enlarged tissue structures in the nose, such as turbinates.

The method of the present invention comprises positioning an electrosurgical instrument adjacent an enlarged body structure so that one or more electrode terminal(s) are brought into at least partial contact or close proximity with the body structure. High frequency voltage is applied between the electrode terminal(s) and one or more return electrode(s) to volumetrically remove at least a portion of the body structure. The electrode terminal(s) may be translated relative to the body structure during or after the application of electrical energy to sculpt a void within the body structure, such as a hole, channel, stripe, crater, or the like. In some embodiments, the electrode terminal(s) are axially translated toward the body structure to bore one or more channel(s) or hole(s) through a portion of the structure. In other embodiments, the electrode terminal(s) are translated across the body structure to form one or more stripe(s) or channel(s). In most embodiments, electrically conducting fluid, such as isotonic saline, is located between the electrode terminal(s) and the body structure. In the bipolar modality, the conducting fluid generates a current flow path between the electrode terminal(s) and one or more return electrode(s). High frequency voltage is then applied between the electrode terminal(s) and the return electrode(s) through the current flow path created by the electrically conducting fluid.

In one aspect of the invention, a method is provided for reducing the volume of enlarged swollen tissue in the patient's nose, such as swollen nasal tissue, mucus membranes, turbinates, polyps, neoplasms or the like. In particular, a turbinate is treated by positioning one or more electrode terminal(s) adjacent to the turbinate, and delivering electrically conductive fluid, such as isotonic saline, to the nasal cavity to substantially surround the electrode terminal(s) with the fluid. Alternatively, a more viscous fluid, such as an electrically conductive gel, may be applied to the target site such that the electrode terminal(s) are submerged within the gel during the procedure. In both embodiments, high frequency voltage is applied between the electrode terminal(s) and one or more return electrode(s) to remove a small tissue segment, channel or hole from the region near or in the turbinates to shrink the turbinates and prevent swelling, due to the formation of scar tissue as the wound heals. The high frequency voltage may be selected to effect a small amount of thermal damage to the walls of the channel or hole to facilitate the formation of scar tissue without extending this thermal damage beyond the immediate region of the target site.

The hole(s) or channel(s) formed by the present invention, typically less than 3 mm diameter, preferably less than 1 mm in diameter, help to shrink the turbinates and prevent swelling. In an exemplary embodiment, an incision is performed (i.e., with a separate instrument, or with the electrosurgical probe of the present invention), so that the mucosa can be lifted before ablating the underlying tissue. This helps to preserve the mucosa and its important function to the nose. Alternatively, the holes may be made directly through mucosa, which should not adversely affect mucosal transport given the small size of the holes formed by the present invention. A more complete description of electrosurgical methods for forming holes or channels in tissue can be found in U.S. Pat. No. 5,683,366, previously incorporated herein by reference.

In a specific configuration, the nasal tissue is removed by molecular dissociation or disintegration processes. In these embodiments, the high frequency voltage applied to the electrode terminal(s) is sufficient to vaporize an electrically conductive fluid (e.g., gel or saline) between the electrode terminal(s) and the tissue. Within the vaporized fluid, a ionized plasma is formed and charged particles (e.g., electrons) are accelerated towards the tissue to cause the molecular breakdown or disintegration of several cell layers of the tissue. This molecular dissociation is accompanied by the volumetric removal of the tissue. The short range of the accelerated charged particles within the plasma layer confines the molecular dissociation process to the surface layer to minimize damage and necrosis to the underlying tissue.

This process can be precisely controlled to effect the volumetric removal of tissue as thin as 10 to 150 microns with minimal heating of, or damage to, surrounding or underlying tissue structures. A more complete description of this phenomena is described in commonly assigned U.S. Pat. No. 5,683,366.

The present invention offers a number of advantages over current microdebrider and laser techniques for nasal surgery. The ability to precisely control the volumetric removal of tissue results in a field of tissue ablation or removal that is very defined, consistent and predictable. Controlling the depth of tissue allows the physician to form a precise channel or hole through the turbinate tissue. This precise heating also helps to minimize or completely eliminate damage to healthy tissue structures, cartilage, bone and/or cranial nerves that are often adjacent the target sinus tissue. In addition, small blood vessels within the nose are simultaneously cauterized and sealed as the tissue is removed to continuously maintain hemostasis during the procedure. This increases the surgeon's field of view, and shortens the length of the procedure. Moreover, since the present invention allows for the use of electrically conductive fluid (contrary to prior art bipolar and monopolar electrosurgery techniques), isotonic saline may be used during the procedure. Saline is the preferred medium for irrigation because it has the same concentration as the body's fluids and, therefore, is not absorbed into the body as much as other fluids.

Apparatus according to the present invention generally include an electrosurgical probe or catheter having a shaft with proximal and distal ends, one or more electrode terminal(s) at the distal end and one or more connectors coupling the electrode terminal(s) to a source of high frequency electrical energy. For treating swollen turbinates, the distal end portion of the shaft will usually have a diameter of less than 3mm, preferably less than 1 mm, to facilitate the formation of small hole(s) or channel(s) within the swollen turbinate tissue. The shaft may additionally include a lens at the distal end coupled to a proximal eye piece for endoscopically viewing the target tissue. Alternatively, the endoscope may be a separate instrument that is introduced through the same or a different opening as the electrosurgical probe.

The apparatus will preferably further include a fluid delivery element for delivering electrically conducting fluid to the electrode terminal(s) and the target site. The fluid delivery element may be located on the probe, e.g., a fluid lumen or tube, or it may be part of a separate instrument. Alternatively, an electrically conducting gel or spray, such as a saline electrolyte or other conductive gel, may be applied the target site. In this embodiment, the apparatus may not have a fluid delivery element. In both embodiments, the electrically conducting fluid will preferably generate a current flow path between the electrode terminal(s) and one or more return electrode(s). In an exemplary embodiment, the return electrode is located on the probe and spaced a sufficient distance from the electrode terminal(s) to substantially avoid or minimize current shorting therebetween and to shield the return electrode from tissue at the target site.

In a specific configuration, the electrosurgical probe will include an electrically insulating electrode support member having a tissue treatment surface at the distal end of the probe. One or more electrode terminal(s) are coupled to, or integral with, the electrode support member such that the electrode terminal(s) are spaced from the return electrode. In one embodiment, the probe includes an electrode array having a plurality of electrically isolated electrode terminals embedded into the electrode support member such that the electrode terminals extend about 0.2 mm to about 10 mm. In this embodiment, the probe will further include one or more lumens for delivering electrically conductive fluid to one or more openings around the tissue treatment surface of the electrode support member. In an exemplary embodiment, the lumen will extend through a fluid tube exterior to the probe shaft that ends proximal to the return electrode.

In another embodiment, an electrosurgical instrument, such as a probe or catheter, comprises a shaft with proximal and distal ends, one or more electrode terminal(s) at the distal end and one or more connectors coupling the electrode terminal(s) to a source of high frequency electrical energy. In this embodiment, the electrode terminal(s) are preferably designed for cutting tissue; i.e., they typically have a distal edge or point. Conventional electrosurgery cuts through tissue by rapidly heating the tissue until cellular fluids explode, producing a cutting effect along the pathway of localized heating. The present invention volumetrically removes the tissue along the cutting pathway in a cool ablation process that minimizes thermal damage to surrounding tissue. The electrode terminal(s) are preferably designed for cutting tissue; i.e., they typically have a distal edge or point. In the exemplary embodiment, the electrode terminal(s) are aligned with each other to form a linear cutting path through the tissue.

DESCRIPTION OF SPECIFIC EMBODIMENTS

Figure 1:
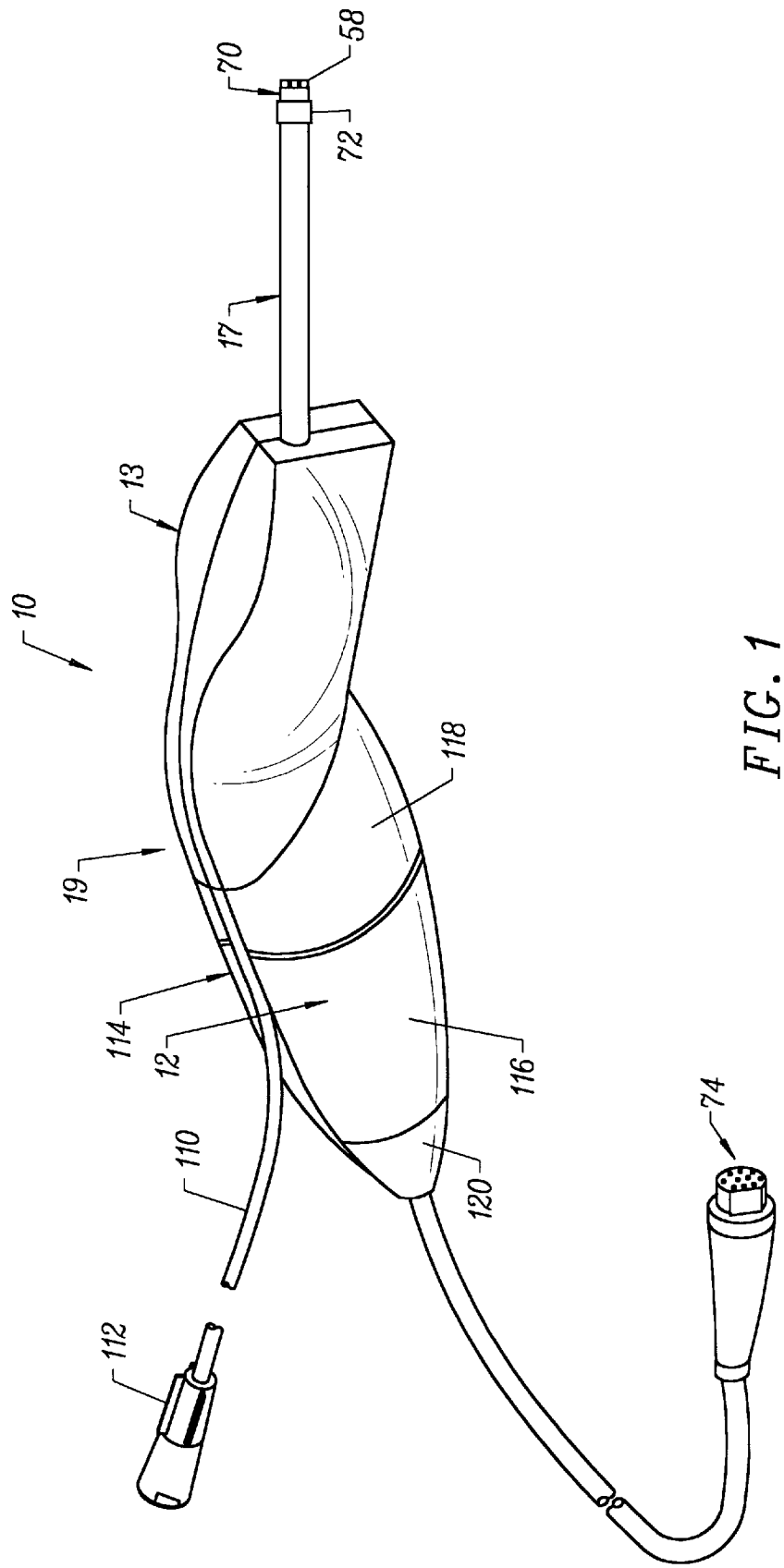
FIG. 1 is a perspective view of an electrosurgical probe for forming holes or channels through tissue, particularly for use in treating turbinates.

The present invention provides systems and methods for selectively applying electrical energy to a target location within or on a patient's body, particularly including tissue in head and neck, such as the ear, mouth, pharynx, larynx, esophagus, nasal cavity and sinuses. These procedures may be performed through the mouth or nose using speculae or gags, or using endoscopic techniques. These procedures may include the removal of swollen tissue, chronically-diseased inflamed and hypertrophic mucus linings, polyps and/or neoplasms from the various anatomical sinuses of the skull, the turbinates and nasal passages, in the tonsil, adenoid, epi-glottic and supra-glottic regions, and salivary glands, submucus resection of the nasal septum, excision of diseased tissue and the like. In other procedures, the present invention may be useful for collagen shrinkage, ablation and/or hemostasis in procedures for treating snoring and obstructive sleep apnea (e.g., soft palate, such as the uvula, or tongue/pharynx stiffening, and midline glossectomies), for gross tissue removal, such as tonsillectomies, adenoidectomies, tracheal stenosis and vocal cord polyps and lesions, or for the resection or ablation of facial tumors or tumors within the mouth and pharynx, such as glossectomies, laryngectomies, acoustic neuroma procedures and nasal ablation procedures.

The present invention may also be useful for cosmetic and plastic surgery procedures in the head and neck. For example, the present invention is particularly useful for ablation and sculpting of cartilage tissue, such as the cartilage within the nose that is sculpted during rhinoplasty procedures. The present invention may also be employed for skin tissue removal and/or collagen shrinkage in the epidermis or dermis tissue in the head and neck, e.g., the removal of pigmentations, vascular lesions (e.g., leg veins), scars, tattoos, etc., and for other surgical procedures on the skin, such as tissue rejuvenation, cosmetic eye procedures (blepharoplasties), wrinkle removal, tightening muscles for facelifts or browlifts, hair removal and/or transplant procedures, etc.

For convenience, the remaining disclosure will be directed specifically to the treatment of enlarged tissue structures within the nose, such as turbinates, but it will be appreciated that the system and method can be applied equally well to procedures involving other tissues of the body, as well as to other procedures including open procedures, intravascular procedures, urology, laparascopy, arthroscopy, thoracoscopy or other cardiac procedures, cosmetic surgery, orthopedics, gynecology, otorhinolaryngology, spinal and neurologic procedures, oncology and the like.

In the present invention, high frequency (RF) electrical energy is applied to one or more electrode terminals in the presence of electrically conductive fluid to remove and/or modify the structure of tissue structures. Depending on the specific procedure, the present invention may be used to: (1) volumetrically remove tissue, bone or cartilage (i.e., ablate or effect molecular dissociation of the tissue structure); (2) form holes, channels, divots or other spaces within tissue (3) cut or resect tissue; (4) shrink or contract collagen connective tissue; and/or (5) coagulate severed blood vessels.

In some procedures, the tissue structures are volumetrically removed or ablated by applying a high frequency voltage difference between one or more electrode terminal (s) and one or more return electrode(s). The voltage difference is sufficient to develop high electric field intensities in the vicinity of the target tissue site, which lead to electric field induced molecular breakdown of target tissue through molecular dissociation (rather than thermal evaporation or carbonization). The tissue structure is volumetrically removed through molecular disintegration of larger organic molecules into smaller molecules and/or atoms, such as hydrogen, oxides of carbon, hydrocarbons and nitrogen compounds. This molecular disintegration completely removes the tissue structure, as opposed to dehydrating the tissue material by the removal of liquid within the cells of the tissue, as is typically the case with electrosurgical desiccation and vaporization.

The high electric field intensities may be generated by applying a high frequency voltage that is sufficient to vaporize an electrically conducting fluid over at least a portion of the electrode terminal(s) in the region between the distal tip of the electrode terminal(s) and the target tissue. The electrically conductive fluid may be a gas or liquid, such as isotonic saline, delivered to the target site, or a viscous fluid, such as a gel, that is located at the target site. In the latter embodiment, the electrode terminal(s) are submersed in the electrically conductive gel during the surgical procedure. Since the vapor layer or vaporized region has a relatively high electrical impedance, it increases the voltage differential between the electrode terminal tip and the tissue and causes ionization within the vapor layer due to the presence of an ionizable species (e.g., sodium when isotonic saline is the electrically conducting fluid). This ionization, under optimal conditions, induces the discharge of energetic electrons and photons from the vapor layer and to the surface of the target tissue. This energy may be in the form of energetic photons (e.g., ultraviolet radiation), energetic particles (e.g., electrons) or a combination thereof. A more detailed description of this cold ablation phenomena, termed Coblation™, can be found in commonly assigned U.S. Pat. No. 5,683,366 the complete disclosure of which is incorporated herein by reference.

The present invention applies high frequency (RF) electrical energy in an electrically conducting fluid environment to remove (i.e., resect, cut or ablate) or contract a tissue structure, and to seal transected vessels within the region of the target tissue. The present invention is particularly useful for sealing larger arterial vessels, e.g., on the order of 1 mm or greater. In some embodiments, a high frequency power supply is provided having an ablation mode, wherein a first voltage is applied to an electrode terminal sufficient to effect molecular dissociation or disintegration of the tissue, and a coagulation mode, wherein a second, lower voltage is applied to an electrode terminal (either the same or a different electrode) sufficient to achieve hemostasis of severed vessels within the tissue. In other embodiments, an electrosurgical probe is provided having one or more coagulation electrode(s) configured for sealing a severed vessel, such as an arterial vessel, and one or more electrode terminals configured for either contracting the collagen fibers within the tissue or removing (ablating) the tissue, e.g., by applying sufficient energy to the tissue to effect molecular dissociation. In the latter embodiments, the coagulation electrode(s) may be configured such that a single voltage can be applied to coagulate with the coagulation electrode(s), and to ablate or contract with the electrode terminal(s). In other embodiments, the power supply is combined with the coagulation probe such that the coagulation electrode is used when the power supply is in the coagulation mode (low voltage), and the electrode terminal(s) are used when the power supply is in the ablation mode (higher voltage).

In the method of the present invention, one or more electrode terminals are brought into close proximity to tissue at a target site, and the power supply is activated in the ablation mode such that sufficient voltage is applied between the electrode terminals and the return electrode to volumetrically remove the tissue through molecular dissociation, as described below. During this process, vessels within the tissue will be severed. Smaller vessels will be automatically sealed with the system and method of the present invention. Larger vessels, and those with a higher flow rate, such as arterial vessels, may not be automatically sealed in the ablation mode. In these cases, the severed vessels may be sealed by activating a control (e.g., a foot pedal) to reduce the voltage of the power supply into the coagulation mode. In this mode, the electrode terminals may be pressed against the severed vessel to provide sealing and/or coagulation of the vessel. Alternatively, a coagulation electrode located on the same or a different probe may be pressed against the severed vessel. Once the vessel is adequately sealed, the surgeon activates a control (e.g., another foot pedal) to increase the voltage of the power supply back into the ablation mode.

The present invention is particularly useful for removing or ablating tissue around nerves, such as spinal or cranial nerves, e.g., the olfactory nerve on either side of the nasal cavity, the optic nerve within the optic and cranial canals, the palatine nerve within the nasal cavity, soft palate, uvula and tonsil, etc. One of the significant drawbacks with the prior art microdebriders and lasers is that these devices do not differentiate between the target tissue and the surrounding nerves or bone. Therefore, the surgeon must be extremely careful during these procedures to avoid damage to the bone or nerves within and around the nasal cavity. In the present invention, the Coblation™ process for removing tissue results in extremely small depths of collateral tissue damage as discussed above. This allows the surgeon to remove tissue close to a nerve without causing collateral damage to the nerve fibers.

In addition to the generally precise nature of the novel mechanisms of the present invention, applicant has discovered an additional method of ensuring that adjacent nerves are not damaged during tissue removal. According to the present invention, systems and methods are provided for distinguishing between the fatty tissue immediately surrounding nerve fibers and the normal tissue that is to be removed during the procedure. Nerves usually comprise a connective tissue sheath, or endoneurium, enclosing the bundles of nerve fibers to protect these nerve fibers. This protective tissue sheath typically comprises a fatty tissue (e.g., adipose tissue) having substantially different electrical properties than the normal target tissue, such as the turbinates, polyps, mucus tissue or the like, that are, for example, removed from the nose during sinus procedures. The system of the present invention measures the electrical properties of the tissue at the tip of the probe with one or more electrode terminal(s). These electrical properties may include electrical conductivity at one, several or a range of frequencies (e.g., in the range from 1kHz to 100 MHz), dielectric constant, capacitance or combinations of these. In this embodiment, an audible signal may be produced when the sensing electrode(s) at the tip of the probe detects the fatty tissue surrounding a nerve, or direct feedback control can be provided to only supply power to the electrode terminal(s) either individually or to the complete array of electrodes, if and when the tissue encountered at the tip or working end of the probe is normal tissue based on the measured electrical properties.

In one embodiment, the current limiting elements (discussed in detail above) are configured such that the electrode terminals will shut down or turn off when the electrical impedance reaches a threshold level. When this threshold level is set to the impedance of the fatty tissue surrounding nerves, the electrode terminals will shut off whenever they come in contact with, or in close proximity to, nerves. Meanwhile, the other electrode terminals, which are in contact with or in close proximity to nasal tissue, will continue to conduct electric current to the return electrode. This selective ablation or removal of lower impedance tissue in combination with the Coblation™ mechanism of the present invention allows the surgeon to precisely remove tissue around nerves or bone.

In addition to the above, applicant has discovered that the Coblation™ mechanism of the present invention can be manipulated to ablate or remove certain tissue structures, while having little effect on other tissue structures. As discussed above, the present invention uses a technique of vaporizing electrically conductive fluid to form a plasma layer or pocket around the electrode terminal(s), and then inducing the discharge of energy from this plasma or vapor layer to break the molecular bonds of the tissue structure. Based on initial experiments, applicants believe that the free electrons within the ionized vapor layer are accelerated in the high electric fields near the electrode tip(s). When the density of the vapor layer (or within a bubble formed in the electrically conducting liquid) becomes sufficiently low (i.e., less than approximately $10^{20}$ atoms/cm$^3$ for aqueous solutions), the electron mean free path increases to enable subsequently injected electrons to cause impact ionization within these regions of low density (i.e., vapor layers or bubbles). Energy evolved by the energetic electrons (e.g., 4 to 5 eV) can subsequently bombard a molecule and break its bonds, dissociating a molecule into free radicals, which then combine into final gaseous or liquid species.

The energy evolved by the energetic electrons may be varied by adjusting a variety of factors, such as: the number of electrode terminals; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Accordingly, these factors can be manipulated to control the energy level of the excited electrons. Since different tissue structures have different molecular bonds, the present invention can be configured to break the molecular bonds of certain tissue, while having too low an energy to break the molecular bonds of other tissue. For example, fatty tissue, (e.g., adipose) tissue has double bonds that require a substantially higher energy level than 4 to 5 eV to break. Accordingly, the present invention in its current configuration generally does not ablate or remove such fatty tissue. Of course, factors may be changed such that these double bonds can be broken (e.g., increasing voltage or changing the electrode configuration to increase the current density at the electrode tips).

In other procedures, e.g., soft palate or tongue/pharynx stiffening, it is desired to shrink or contract collagen connective tissue at the target site. In addition, it may be desirable to stiffen the turbinates after a portion of the tissue has been removed. In these procedures, the RF energy heats the tissue directly by virtue of the electrical current flow therethrough, and/or indirectly through the exposure of the tissue to fluid heated by RF energy, to elevate the tissue temperature from normal body temperatures (e.g., 37° C.) to temperatures in the range of 45° C. to 90° C., preferably in the range from about 60° C. to 70° C. Thermal shrinkage of collagen fibers occurs within a small temperature range which, for mammalian collagen is in the range from 60° C. to 70° C. (Deak, G., et al., "The Thermal Shrinkage Process of Collagen Fibres as Revealed by Polarization Optical Analysis of Topooptical Staining Reactions," Acta Morphologica Acad. Sci. of Hungary, Vol. 15(2), pp 195–208, 1967). Collagen fibers typically undergo thermal shrinkage in the range of 60° C. to about 70° C. Previously reported research has attributed thermal shrinkage of collagen to the cleaving of the internal stabilizing cross-linkages within the collagen matrix (Deak, ibid). It has also been reported that when the collagen temperature is increased above 70° C, the collagen matrix begins to relax again and the shrinkage effect is increased above 70° C., the collagen matrix begins to relax again and the shrinkage effect is reversed resulting in no net shrinkage (Allaink, J. C., et al., "Isometric Tensions Developed During the Hydrothermal Swelling of Rat Skin," Connective Tissue Research, Vol. 7, pp 127–133, 1980). Consequently, the controlled heating of tissue to a precise depth is critical to the achievement of therapeutic collagen shrinkage. A more detailed description of collagen shrinkage can be found in U.S. patent application Ser. No. 08/942,580, filed on Oct. 2, 1997, (Attorney Docket No. 16238-001300).

The preferred depth of heating to effect the shrinkage of collagen in the heated region (i.e., the depth to which the tissue is elevated to temperatures between 60° C. to 70° C.) generally depends on (1) the thickness of the tissue, (2) the location of nearby structures (e.g., nerves) that should not be exposed to damaging temperatures, and/or (3) the location of the collagen tissue layer within which therapeutic shrinkage is to be effected. The depth of heating is usually in the range from 0 to 3.5 mm. In the case of collagen within the soft palate or uvula, the depth of heating is preferably in the range from about 0.5 to about 3.5 mm.

The electrosurgical instrument (e.g., probe or catheter) will comprise a shaft or a handpiece having a proximal end and a distal end which supports one or more electrode terminal(s). The shaft or handpiece may assume a wide variety of configurations, with the primary purpose being to mechanically support the active electrode and permit the treating physician to manipulate the electrode from a proximal end of the shaft. The shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode array. The shaft will usually include a plurality of wires or other conductive elements running axially therethrough to permit connection of the electrode array to a connector at the proximal end of the shaft.

For procedures within the nose, the shaft will have a suitable diameter and length to allow the surgeon to reach the target site (e.g., a blockage or enlarged turbinate in the nasal cavity) by delivering the probe shaft through one of the nasal passages or another opening (e.g., an opening in the eye or through an opening surgically creating during the procedure). Thus, the shaft will usually have a length in the range of about 5–25cm, and a diameter in the range of about 0.5 to 5 mm. For procedures requiring the formation of a small hole or channel in tissue, such as treating swollen turbinates, the shaft diameter will usually be less than 3 mm, preferably less than about 1 mm. Likewise, for procedures in the ear, the shaft should have a length in the range of about 3 to 20 cm, and a diameter of about 0.3 to 5 mm. For procedures in the mouth or upper throat, the shaft will have any suitable length and diameter that would facilitate handling by the surgeon. For procedures in the lower throat, such as laryngectomies, the shaft will be suitably designed to access the larynx. For example, the shaft may be flexible, or have a distal bend to accommodate the bend in the patient's throat. In this regard, the shaft may be a rigid shaft having a specifically designed bend to correspond with the geometry of the mouth and throat, or it may have a flexible distal end, or it may be part of a catheter. In any of these embodiments, the shaft may also be introduced through rigid or flexible endoscopes. Specific shaft designs will be described in detail in connection with the figures hereinafter.

The current flow path between the electrode terminal(s) and the return electrode(s) may be generated by submerging the tissue site in an electrical conducting fluid (e.g., within a viscous fluid, such as an electrically conductive gel) or by directing an electrically conducting fluid along a fluid path to the target site (i.e., a liquid, such as isotonic saline, or a gas, such as argon). This latter method is particularly effective in a dry environment (i.e., the tissue is not submerged in fluid) because the electrically conducting fluid provides a suitable current flow path from the electrode terminal to the return electrode. A more complete description of an exemplary method of directing electrically conducting fluid between the active and return electrodes is described in U.S. Pat. No. 5,697,800, previously incorporated herein by reference.

In some procedures, it may also be necessary to retrieve or aspirate the electrically conductive fluid after it has been directed to the target site. For example, in procedures in the nose, mouth or throat, it may be desirable to aspirate the fluid so that it does not flow down the patient's throat. In addition, it may be desirable to aspirate small pieces of tissue that are not completely disintegrated by the high frequency energy, or other fluids at the target site, such as blood, mucus, the gaseous products of ablation, etc. Accordingly, the system of the present invention will usually include a suction lumen in the probe, or on another instrument, for aspirating fluids from the target site.

The present invention may use a single active electrode terminal or an electrode array distributed over a contact surface of a probe. In the latter embodiment, the electrode array usually includes a plurality of independently current-limited and/or power-controlled electrode terminals to apply electrical energy selectively to the target tissue while limiting the unwanted application of electrical energy to the surrounding tissue and environment resulting from power dissipation into surrounding electrically conductive liquids, such as blood, normal saline, electrically conductive gel and the like. The electrode terminals may be independently current-limited by isolating the terminals from each other and connecting each terminal to a separate power source that is isolated from the other electrode terminals. Alternatively, the electrode terminals may be connected to each other at either the proximal or distal ends of the probe to form a single wire that couples to a power source.

In one configuration, each individual electrode terminal in the electrode array is electrically insulated from all other electrode terminals in the array within said probe and is connected to a power source which is isolated from each of the other electrode terminals in the array or to circuitry which limits or interrupts current flow to the electrode terminal when low resistivity material (e.g., blood, electrically conductive saline irrigant or electrically conductive gel) causes a lower impedance path between the return electrode and the individual electrode terminal. The isolated power sources for each individual electrode terminal may be separate power supply circuits having internal impedance characteristics which limit power to the associated electrode terminal when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the electrode terminals through independently actuatable switches, or by independent current limiting elements, such as inductors, capacitors, resistors and/or combinations thereof. The current limiting elements may be provided in the probe, connectors, cable, controller or along the conductive path from the controller to the distal tip of the probe. Alternatively, the resistance and/or capacitance may occur on the surface of the active electrode terminal(s) due to oxide layers which form selected electrode terminals (e.g., titanium or a resistive coating on the surface of metal, such as platinum).

The tip region of the probe may comprise many independent electrode terminals designed to deliver electrical energy in the vicinity of the tip. The selective application of electrical energy to the conductive fluid is achieved by connecting each individual electrode terminal and the return electrode to a power source having independently controlled or current limited channels. The return electrode(s) may comprise a single tubular member of conductive material proximal to the electrode array at the tip which also serves as a conduit for the supply of the electrically conducting fluid between the active and return electrodes. Alternatively, the probe may comprise an array of return electrodes at the distal tip of the probe (together with the active electrodes) to maintain the electric current at the tip. The application of high frequency voltage between the return electrode(s) and the electrode array results in the generation of high electric field intensities at the distal tips of the electrode terminals with conduction of high frequency current from each individual electrode terminal to the return electrode. The current flow from each individual electrode terminal to the return electrode(s) is controlled by either active or passive means, or a combination thereof, to deliver electrical energy to the surrounding conductive fluid while minimizing energy delivery to surrounding (non-target) tissue.

The application of a high frequency voltage between the return electrode(s) and the electrode terminal(s) for appropriate time intervals effects cutting, removing, ablating, shaping, contracting or otherwise modifying the target tissue. The tissue volume over which energy is dissipated (i.e., a high current density exists) may be precisely controlled, for example, by the use of a multiplicity of small electrode terminals whose effective diameters or principal dimensions range from about 5 mm to 0.01 mm, preferably from about 2 mm to 0.05 mm, and more preferably from about 1 mm to 0.1 mm. Electrode areas for both circular and non-circular terminals will have a contact area (per electrode terminal) below 25 mm$^2$, preferably being in the range from 0.0001 mm$^2$ to 1 mm$^2$, and more preferably from 0.005 mm$^2$ to 0.5 mm$^2$. The circumscribed area of the electrode array is in the range from 0.25 mm$^2$ to 75 mm$^2$, preferably from 0.5 mm$^2$ to 40mm$^2$, and will usually include at least two isolated electrode terminals, preferably at least five electrode terminals, often greater than 10 electrode terminals and even 50 or more electrode terminals, disposed over the distal contact surfaces on the shaft. The use of small diameter electrode terminals increases the electric field intensity and reduces the extent or depth of tissue heating as a consequence of the divergence of current flux lines which emanate from the exposed surface of each electrode terminal.

The area of the tissue treatment surface can vary widely, and the tissue treatment surface can assume a variety of geometries, with particular areas and geometries being selected for specific applications. Active electrode surfaces can have areas in the range from 0.25 mm$^2$ to 75 mm$^2$, usually being from about 0.5 mm$^2$ to 40 mm$^2$. The geometries can be planar, concave, convex, hemispherical, conical, linear "in-line" array or virtually any other regular or irregular shape. Most commonly, the active electrode(s) or electrode terminal(s) will be formed at the distal tip of the electrosurgical probe shaft, frequently being planar, disk-shaped, or hemispherical surfaces for use in reshaping procedures or being linear arrays for use in cutting. Alternatively or additionally, the active electrode(s) may be formed on lateral surfaces of the electrosurgical probe shaft (e.g., in the manner of a spatula), facilitating access to certain body structures in endoscopic procedures.

In the representative embodiments, the electrode terminals comprise substantially rigid wires protruding outward from the tissue treatment surface of the electrode support member. Usually, the wires will extend about 0.1 to 4.0 mm, preferably about 0.2 to 1 mm, from the distal surface of the support member. In the exemplary embodiments, the electrosurgical probe includes between about two to fifty electrically isolated electrode terminals, and preferably between about three to twenty electrode terminals.

The electrically conducting fluid should have a threshold conductivity to provide a suitable conductive path between the return electrode(s) and the electrode terminal(s). The electrical conductivity of the fluid (in units of milliSiemans per centimeter or mS/cm) will usually be greater than 0.2 mS/cm, preferably will be greater than 2 mS/cm and more preferably greater than 10 mS/cm. In an exemplary embodiment, the electrically conductive fluid is isotonic saline, which has a conductivity of about 17mS/cm.

In some embodiments, the electrode support and the fluid outlet may be recessed from an outer surface of the probe or handpiece to confine the electrically conductive fluid to the region immediately surrounding the electrode support. In addition, the shaft may be shaped so as to form a cavity around the electrode support and the fluid outlet. This helps to assure that the electrically conductive fluid will remain in contact with the electrode terminal(s) and the return electrode(s) to maintain the conductive path therebetween. In addition, this will help to maintain a vapor or plasma layer betweed between the return electrode(s) and the electrode array electrode terminal(s) and the tissue at the treatment site throughout the procedure, which reduces the thermal damage that might otherwise occur if the vapor layer were extinguished due to a lack of conductive fluid. Provision of the electrically conductive fluid around the target site also helps to maintain the tissue temperature at desired levels.

The voltage applied between the return electrode(s) and the electrode array will be at high or radio frequency, typically between about 5 kHz and 20 MHz, usually being between about 30 kHz and 2.5 MHz, preferably being between about 50 kHz and 500 kHz, more preferably less than 350 kHz, and most preferably between about 100 kHz and 200 kHz. The RMS (root mean square) voltage applied will usually be in the range from about 5 volts to 1000 volts, preferably being in the range from about 10 volts to 500 volts depending on the electrode terminal size, the operating frequency and the operation mode of the particular procedure or desired effect on the tissue (i.e., contraction, coagulation or ablation). Typically, the peak-to-peak voltage will be in the range of 10 to 2000 volts, preferably in the range of 20 to 1200 volts and more preferably in the range of about 40 to 800 volts (again, depending on the electrode size, the operating frequency and the operation mode).

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with e.g., lasers claiming small depths of necrosis, which are generally pulsed about 10 to 20 Hz). In addition, the duty cycle (i.e., cumulative time in any one-second interval that energy is applied) is on the order of about 50% or the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of tagarted tissue being heated, and/or the maximum allowed temperature selected for the probe tip. The power source allows the user to select the voltage level according to the specific requirements of a particular otorhinolaryngology procedure, arthroscopic surgery, dermatological procedure, ophthalmic procedures, open surgery or other endoscopic surgery procedure. A description of a suitable power source can be found in Provisional Application No. 60/075,059 filed Feb. 18, 1998, previously incorporated herein by reference.

The power source may be current limited or otherwise controlled so that undesired heating of the target tissue or surrounding (non-target) tissue does not occur. In a presently preferred embodiment of the present invention, current limiting inductors are placed in series with each independent electrode terminal, where the inductance of the inductor is in the range of 10uH to 50,000uH, depending on the electrical properties of the target tissue, the desired tissue heating rate and the operating frequency. Alternatively, capacitor-inductor (LC) circuit structures may be employed, as described previously in co-pending PCT application No. PCT/US94/05168, the complete disclosure of which is incorporated herein by reference. Additionally, current limiting resistors may be selected. Preferably, these resistors will have a large positive temperature coefficient of resistance so that, as the current level begins to rise for any individual electrode terminal in contact with a low resistance medium (e.g., saline irrigant or conductive gel), the resistance of the current limiting resistor increases significantly, thereby minimizing the power delivery from said electrode terminal into the low resistance medium (e.g., saline irrigant or conductive gel).

It should be clearly understood that the invention is not limited to electrically isolated electrode terminals, or even to a plurality of electrode terminals. For example, the array of active electrode terminals may be connected to a single lead that extends through the probe shaft to a power source of high frequency current. Alternatively, the probe may incorporate a single electrode that extends directly through the probe shaft or is connected to a single lead that extends to the power source. The active electrode may have a ball shape (e.g., for tissue vaporization and desiccation), a twizzle shape (for vaporization and needle-like cutting), a spring shape (for rapid tissue debulking and desiccation), a twisted metal shape, an annular or solid tube shape or the like. Alternatively, the electrode may comprise a plurality of filaments, a rigid or flexible brush electrode (for debulking a tumor, such as a fibroid, bladder tumor or a prostate adenoma), a side-effect brush electrode on a lateral surface of the shaft, a coiled electrode or the like. In one embodiment, the probe comprises a single active electrode terminal that extends from an atraumatic insulating member, e.g. at the distal end of the probe. The active electrode member tapers toward its distal end, and may form a sharp point at the distal end. The atraumatic insulating member may be movable relative to the active electrode so that the insulating member can be advanced and retracted to shield and/or expose the active electrode from the surrounding tissue.

Figure 2:
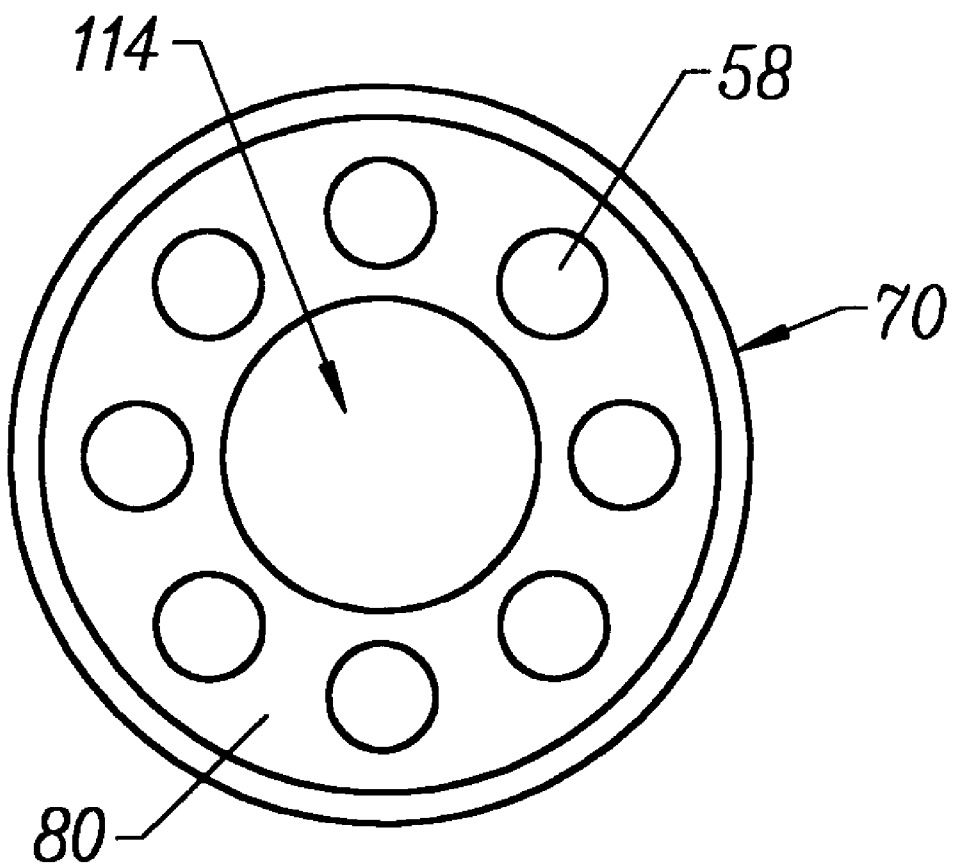
FIG. 2 is a cross-sectional view of a distal shaft portion of the electrosurgical probe of FIG. 1.

Referring now to FIGS. 1 and 2, an exemplary electrosurgical probe 10 comprises a handle 19, which preferably comprises a disposable distal portion 13 removably coupled to a proximal reusable portion 12, and an elongate shaft 17 extending from distal portion 13 of handle 19. Shaft 17 is also disposable, and preferably removably coupled to distal portion 13 of the handle. The proximal and distal portions of handle 12 typically comprise a plastic material that is easily molded into a suitable shape for handling by the surgeon. Handle 19 defines an inner cavity (not shown) that houses the electrical connections 74 (discussed below in reference to FIG. 7), and provides a suitable interface for connection to an electrical connecting cable 34 (see FIG. 3). In the exemplary embodiment, the proximal portion of handle 19 is constructed so that it can be re-used by sterilizing handle 19 between surgical procedures. However, it should be understood that both the proximal and distal portions of handle 19 may be reusable, or both of these handle portions may be disposable, if desired.

Shaft 17 is preferably sized to provide endoscopic access to the nasal cavity. Accordingly, shaft 17 preferably has a length in the range of about 4 to 25 cm and a diameter less than 1 cm. For treating turbinates, the shaft 17 will also preferably be sized for forming small holes or channels in the turbinates and, therefore, will have a diameter less than 3 mm, preferably less than about 1 mm. Alternatively, shaft 17 may have a distal portion that is smaller than the rest of shaft for forming such holes. As shown in FIG. 1, shaft 17 includes an electrically insulating electrode support member 70 extending from the distal end of shaft 17 (usually about 0.5 to 20 mm) to provide support for a plurality of electrically isolated electrode terminals 58. Alternatively, electrode support member 70 may be recessed from the distal end of shaft 17 to help confine the electrically conductive fluid around the electrode terminals 58 during the surgical procedure, as discussed above. Electrode support member 70 has a substantially planar tissue treatment surface 80 (see FIG. 2) that may be perpendicular to the longitudinal axis of shaft 17 as depicted, or it may be disposed at an angle of about 10 to 90 degrees to facilitate handling by the surgeon.

In the embodiment shown in FIGS. 1 and 2, probe 10 includes an annular return electrode 72 for completing the current path between electrode terminals 58 and a high frequency power supply 28. Return electrode 72 is spaced proximally from electrode terminal(s) 58 a sufficient distance to avoid arcing therebetween. In addition, return electrode 72 is positioned such that, when electrode terminal(s) 58 are brought adjacent a tissue structure, return electrode 72 is spaced away from the tissue structure so that the tissue structure cannot, at least by itself, complete the current flow path between electrode terminal(s) 58 and return electrode 72.

To complete the current path between electrode terminals 58 and return electrode 72, electrically conducting fluid (e.g., isotonic saline or electrically conducting gel) is located between the active and return electrodes during a surgical procedure. In the representative embodiment, probe 10 includes a fluid tube 110 (FIG. 1) for delivering electrically conductive fluid to the target site. Fluid tube 110 is sized to extend through a groove 114 in handle 11 and through an inner cavity (not shown) in shaft 17 to a distal opening 114 (FIG.2) located adjacent electrode support member 70. Tube 110 preferably extends all the way through the inner cavity to opening 114 to eliminate any possible fluid ingress into the cavity. As shown in FIG. 1, fluid tube 110 includes a proximal connector 112 for coupling to an electrically conductive fluid source 21 (see FIG. 3). Probe 10 will also include a valve or equivalent structure for controlling the flow rate of the electrically conducting fluid to the target site. In the representative embodiment, handle 19 comprises a main body 118, 120 and a rotatable sleeve 116 for controlling fluid flow through tube 110. Rotation of sleeve 116 crimps tube 110 to limit or complete shut off flow therethrough. Of course, this fluid control may be provided by a variety of other input and valve devices, such as switches, buttons, etc.

In alternative embodiments, the fluid path may be directly formed in probe 10 by, for example, a central inner lumen or an annular gap (not shown) within the handle and the shaft. This inner lumen may be formed near the perimeter of the probe 10 such that the electrically conducting fluid tends to flow radior it may be formes the target site, or it may be formed towards the center of probe 10 so that the fluid flows radially outward. In addition, the electrically conducting fluid may be delivered from a fluid delivery element (not shown) that is separate from probe 10. In arthroscopic surgery, for example, the body cavity will be flooded with isotonic saline and the probe 10 will be introduced into this flooded cavity. Electrically conducting fluid will be continually resupplied to maintain the conduction path between return electrode 72 and electrode terminals 58. A more complete description of alternative electrosurgical probes incorporating one or more fluid lumen(s) can be found in U.S. Pat. No. 5,697,281,previously incorporated herein by reference.

Referring to FIG. 2, electrically isolated electrode terminals 58 are circumferentially spaced around fluid opening 114 at the tissue treatment surface 80 of electrode support member 70. In the representative embodiment, the tissue treatment surface 80 has a circular cross-sectional shape with a diameter of about 0.2 to 3 mm, usually less than 1 mm. The individual electrode terminals 58 have the dimensions described above, and preferably extend about 0.05 to 4.0 mm from tissue treatment surface 80. Of course, the electrode terminals 58 may be substantially flush with surface 80 or the terminals may be recessed from this surface. For example, the electrode terminals 58 may be recessed by a distance from 0.01 mm to 1 mm, preferably 0.01 mm to 0.2 mm. In one embodiment of the invention, the electrode terminals are axially adjustable relative to the tissue treatment surface so that the surgeon can adjust the distance between the surface and the electrode terminals.

Figure 3:
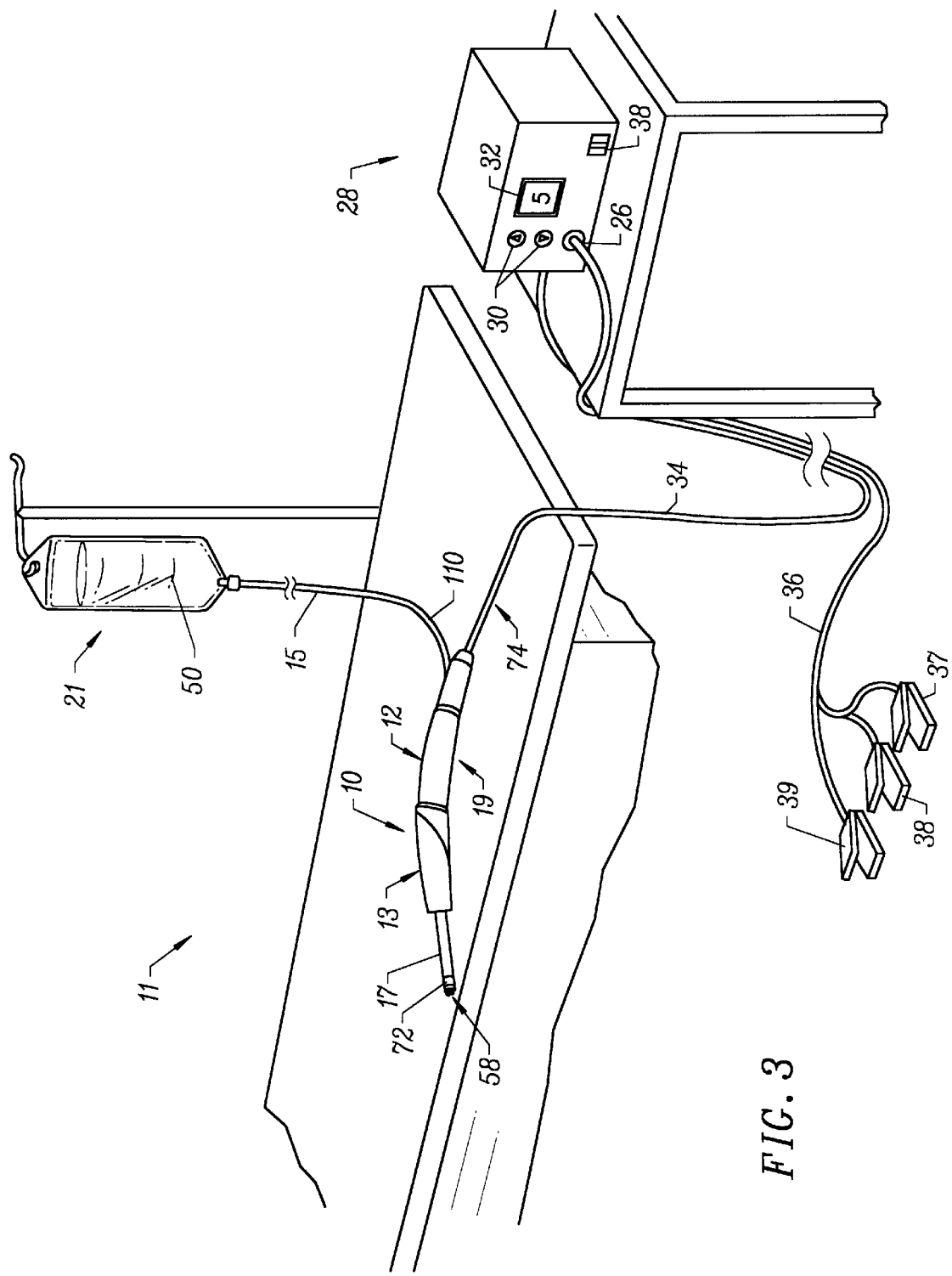
FIG. 3 is a perspective view of an electrosurgical system incorporating a power supply and an electrosurgical probe for tissue ablation, resection, incision, contraction and for vessel hemostasis according to the present invention.

Referring to FIG. 3, an exemplary electrosurgical system 11 for treatment of tissue in the head and neck will now be described in detail. Electrosurgical system 11 generally comprises electrosurgical handpiece or probe 10 (see FIGS. 1 and 2) connected to a power supply 28 for providing high frequency voltage to a target site and a fluid source 21 for supplying electrically conducting fluid 50 to probe 10. In addition, electrosurgical system 11 may include an endoscope (not shown) with a fiber optic head light for viewing the surgical site, particularly in sinus procedures or procedures in the ear or the back of the mouth. The endoscope may be integral with probe 10, or it may be part of a separate instrument. The system 11 may also include a vacuum source (not shown) for coupling to a suction lumen or tube (not shown) in the probe 10 for aspirating the target site.

As shown, a connecting cable 34 has a connector 26 for electrically coupling the electrode terminals 58 and return electrode 72 on probe 10 to power supply 28. The electrode terminals 58 are electrically isolated from each other and each of the terminals 58 is connected to an active or passive control network within power supply 28 by means of a plurality of individually insulated conductors (not shown). A fluid supply tube 15 is connected to fluid tube 110 of probe 10 for supplying electrically conducting fluid 50 to the target site.

Power supply 28 has an operator controllable voltage level adjustment 30 to change the applied voltage level, which is observable at a voltage level display 32. Power supply 28 also includes first, second and third foot pedals 37, 38, 39 and a cable 36 which is removably coupled to power supply 28. The foot pedals 37, 38, 39 allow the surgeon to remotely adjust the energy level applied to electrode terminals 58. In an exemplary embodiment, first foot pedal 37 is used to place the power supply into the "ablation" mode and second foot pedal 38 places power supply 28 into a "subablation" mode (i.e., contraction, coagulation or other types of tissue modification without volumetric tissue removal). The third foot pedal 39 allows the user to adjust the voltage level within the "ablation" mode. In the ablation mode, a sufficient voltage is applied to the electrode terminals to establish the requisite conditions for molecular dissociation of the tissue (i.e., vaporizing a portion of the electrically conductive fluid, ionizing charged particles within the vapor layer and accelerating these charged particles against the tissue). As discussed above, the requisite voltage level for ablation will vary depending on the number, size, shape and spacing of the electrodes, the distance in which the electrodes extend from the support member, etc. Once the surgeon places the power supply in the "ablation" mode, voltage level adjustment 30 or third foot pedal 39 may be used to adjust the voltage level to adjust the degree or aggressiveness of the ablation.

Of course, it will be recognized that the voltage and modality of the power supply may be controlled by other input devices. However, applicant has found that foot pedals are convenient methods of controlling the power supply while manipulating the probe during a surgical procedure.

In the subablation mode, the power supply 28 applies a low enough voltage to the electrode terminals to avoid vaporization of the electrically conductive fluid and subsequent molecular dissociation of the tissue. The surgeon may automatically toggle the power supply between the ablation and subablation modes by alternatively stepping on foot pedals 37, 38, respectively. This allows, for example, the surgeon to quickly move between coagulation and ablation in situ, without having to remove his/her concentration from the surgical field or without having to request an assistant to switch the power supply. By way of example, as the surgeon is sculpting soft tissue in the ablation mode, the probe typically will simultaneously seal and/or coagulation small severed vessels within the tissue. However, larger vessels, or vessels with high fluid pressures (e.g., arterial vessels) may not be sealed in the ablation mode. Accordingly, the surgeon can simply step on foot pedal 38, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by stepping on foot pedal 37.

Figure 4:
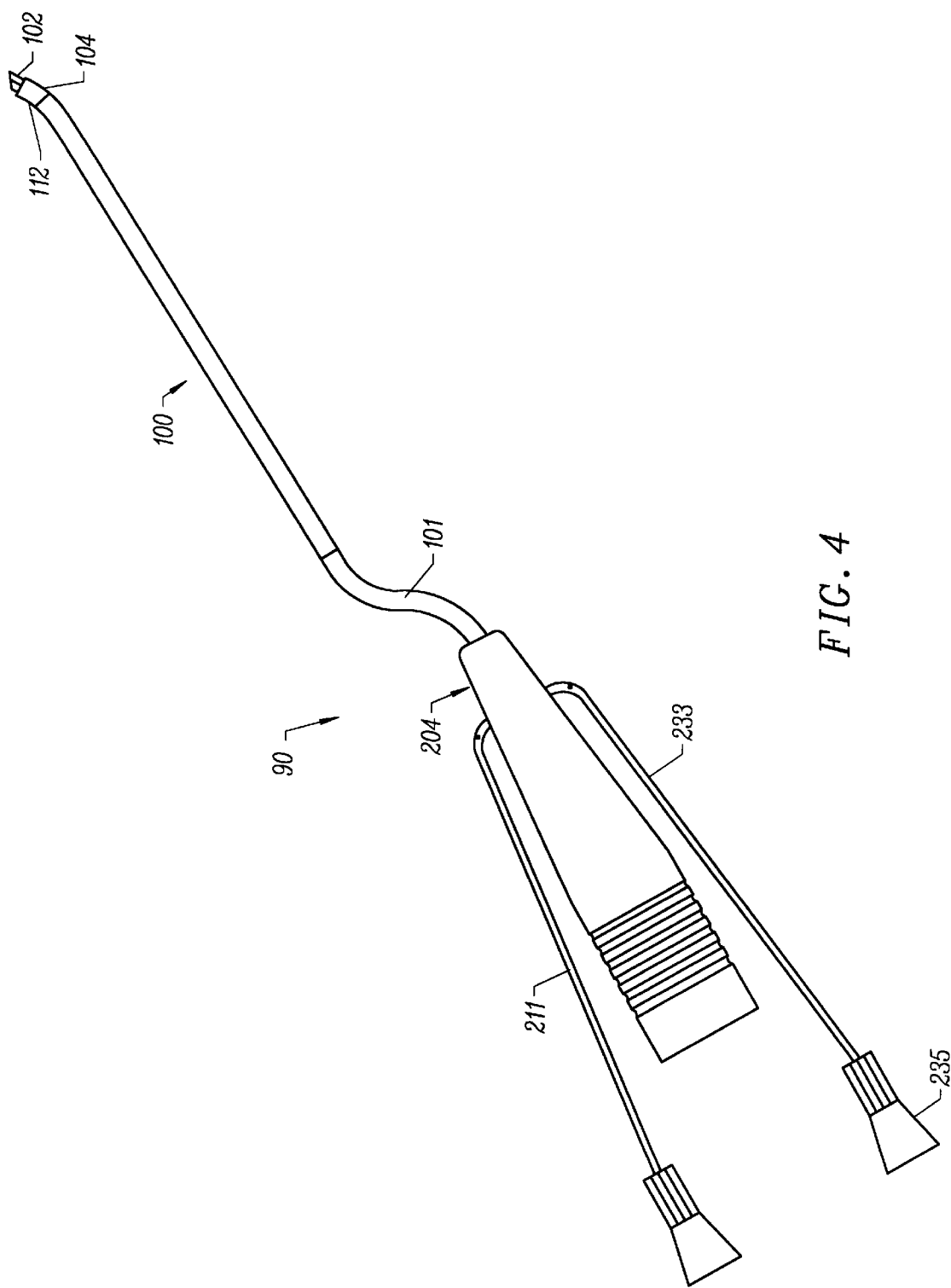
FIG. 4 is a side view of an alternative electrosurgical probe according to the present invention.

FIGS. 4–7 illustrate an alternative electrosurgical probe 90 constructed according to the principles of the present invention for treatment of turbinates, or for other procedures, such as functional endoscopic sinus surgery (FESS). As shown in FIG. 4, probe 90 generally includes an elongated shaft 100 which may be flexible or rigid, a handle 204 coupled to the proximal end of shaft 100 and an electrode support member 102 coupled to the distal end of shaft 100. Shaft 100 preferably includes a bend 101 that allows the distal section of shaft 100 to be offset from the proximal section and handle 204. This offset facilitates procedures that require an endoscope, such as FESS, because the endoscope can, for example, be introduced through the same nasal passage as the shaft 100 without interference between handle 204 and the eyepiece of the endoscope. Shaft 100 preferably comprises a plastic material that is easily molded into the shape shown in FIG. 4.

Figure 8A:
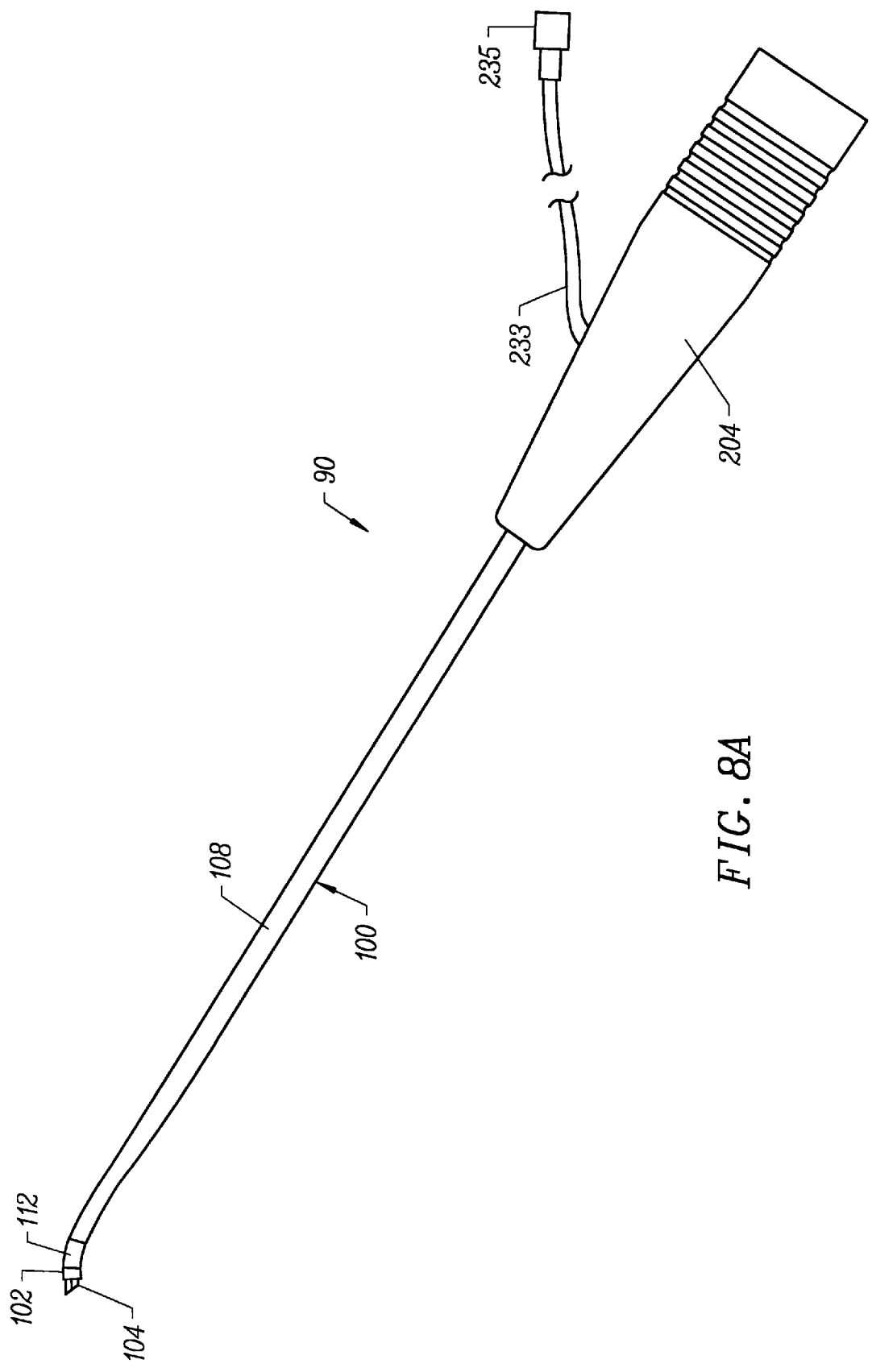
FIGS. 8A and 8B are perspective and end views, respectively, of an alternative electrosurgical probe incorporating an inner fluid lumen.

In an alternative embodiment (see FIG. 8A), shaft 100 comprises an electrically conducting material, usually metal, which is selected from the group comprising tungsten, stainless steel alloys, platinum or its alloys, titanium or its alloys, molybdenum or its alloys, and nickel or its alloys. In this embodiment, shaft 100 includes an electrically insulating jacket 108, which is typically formed as one or more electrically insulating sheaths or coatings, such as polytetrafluoroethylene, polyimide, and the like. The provision of the electrically insulating jacket over the shaft prevents direct electrical contact between these metal elements and any adjacent body structure or the surgeon. Such direct electrical contact between a body structure (e.g., tendon) and an exposed electrode could result in unwanted heating and necrosis of the structure at the point of contact causing necrosis.

Handle 204 typically comprises a plastic material that is easily molded into a suitable shape for handling by the surgeon. Handle 204 defines an inner cavity (not shown) that houses the electrical connections 250 (FIG. 7), and provides a suitable interface for connection to an electrical connecting cable 34 (see FIG. 3). Electrode support member 102 extends from the distal end of shaft 100 (usually about 1 to 20 mm), and provides support for a plurality of electrically isolated electrode terminals 104 (see FIGS. 5 and 6). As shown in FIG. 4, a fluid tube 233 extends through an opening in handle 204, and includes a connector 235 for connection to a fluid supply source, for supplying electrically conductive fluid to the target site. Depending on the configuration of the distal surface of shaft 100, fluid tube 233 may extend through a single lumen (not shown) in shaft 100, or it may be coupled to a plurality of lumens (also not shown) that extend through shaft 100 to a plurality of openings at its distal end. In the representative embodiment, fluid tube 233 extends along the exterior of shaft 100 to a point just proximal of return electrode 112 (see FIG. 6). In this embodiment, the fluid is directed through an opening 237 past return electrode 112 to the electrode terminals 104. Probe 90 may also include a valve 17 (FIG. 3) or equivalent structure for controlling the flow rate of the electrically conducting fluid to the target site.

As shown in FIG. 4, the distal portion of shaft 100 is preferably bent to improve access to the operative site of the tissue being treated. Electrode support member 102 has a substantially planar tissue treatment surface 212 (FIGS. 5 and 6) that is usually at an angle of about 10 to 90 degrees relative to the longitudinal axis of shaft 100, preferably about 30 to 60 degrees and more preferably about 45 degrees. In alternative embodiments, the distal portion of shaft 100 comprises a flexible material which can be deflected relative to the longitudinal axis of the shaft. Such deflection may be selectively induced by mechanical tension of a pull wire, for example, or by a shape memory wire that expands or contracts by externally applied temperature changes.

The bend in the distal portion of shaft 100 is particularly advantageous in the treatment of sinus tissue as it allows the surgeon to reach the target tissue within the nose as the shaft 100 extends through the nasal passage. Of course, it will be recognized that the shaft may have different angles depending on the procedure. For example, a shaft having a 90° bend angle may be particularly useful for accessing tissue located in the back portion of the mouth and a shaft having a 10° to 30° bend angle may be useful for accessing tissue near or in the front portion of the mouth or nose In the embodiment shown in FIGS. 4–7, probe 90 includes a return electrode 112 for completing the current path between electrode terminals 104 and a high frequency power supply 28 (see FIG. 3). As shown, return electrode 112 preferably comprises an annular conductive band coupled to the distal end of shaft 100 slightly proximal to tissue treatment surface 212 of electrode support member 102, typically about 0.5 to 10 mm and more preferably about 1 to 10 mm. Return electrode 112 is coupled to a connector 258 that extends to the proximal end of probe 10, where it is suitably connected to power supply 10 (FIG. 3).

Figure 5:
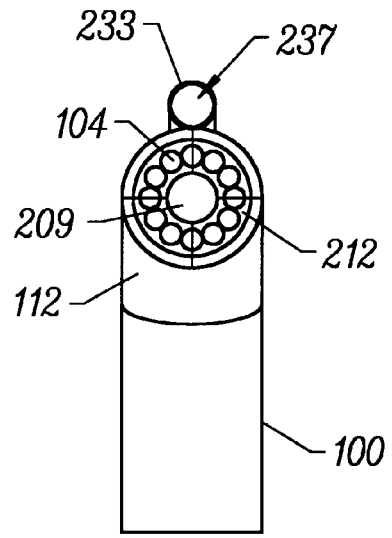
FIG. 5 is an end view of the probe of FIG. 4.
Figure 6:
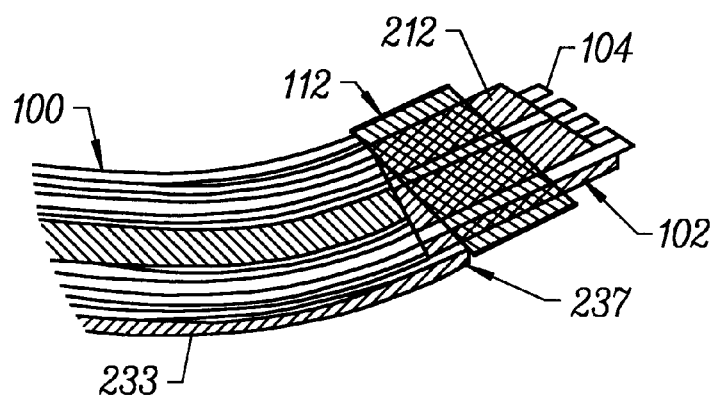
FIG. 6 is a cross sectional view of the electrosurgical probe of FIG. 4.

Referring to FIG. 5, the probe includes a single, larger opening 209 in the center of tissue treatment surface 212, and a plurality of electrode terminals 104 (e.g., about 3–15) around the perimeter of surface 212 (see FIG. 5). Alternatively, the probe may include a single, annular, or partially annular, electrode terminal at the perimeter of the tissue treatment surface. The central opening 209 is coupled to a suction lumen (not shown) within shaft 100 and a suction tube 211 (FIG. 4) for aspirating tissue, fluids and/or gases from the target site. In this embodiment, the electrically conductive fluid generally flows radially inward past electrode terminals 104 and then back through the opening 209. Aspirating the electrically conductive fluid during surgery allows the surgeon to see the target site, and it prevents the fluid from flowing into the patient's body, e.g., through the sinus passages, down the patient's throat or into the ear canal. This aspiration should be controlled, however, so that the conductive fluid maintains a conductive path between the active electrode terminal(s) and the return electrode. In some embodiments, the probe 20 will also include one or more aspiration electrode(s) (not shown) coupled to the aspiration lumen for inhibiting clogging during aspiration of tissue fragments from the surgical site. A more complete description of these embodiments can be found in commonly assigned co-pending application Ser. No. 09/010,382, filed Jan. 21, 1998 (Attorney Docket No. A-6), the complete disclosure of which is incorporated herein by reference for all purposes.

Figure 8B:
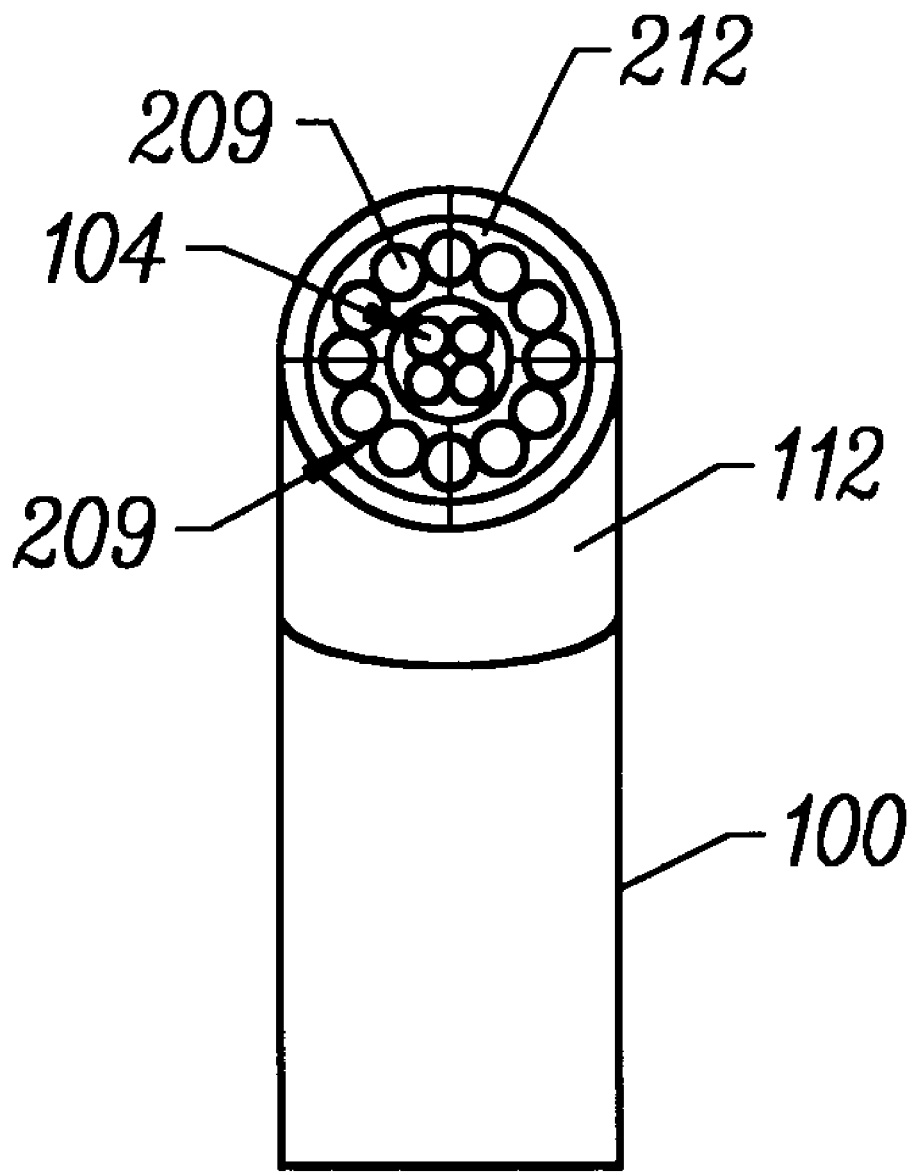

Of course, it will be recognized that the distal tip of probe may have a variety of different configurations. For example, the probe may include a plurality of openings 209 around the outer perimeter of tissue treatment surface 212 (see FIG. 8B). In this embodiment, the electrode terminals 104 extend from the center of tissue treatment surface 212 spaced radially inward from openings 209. The openings are suitably coupled to fluid tube 233 for delivering electrically conductive fluid to the target site, and suction tube 211 for aspirating the fluid after it has completed the conductive path between the return electrode 112 and the electrode terminals 104.

Figure 7:
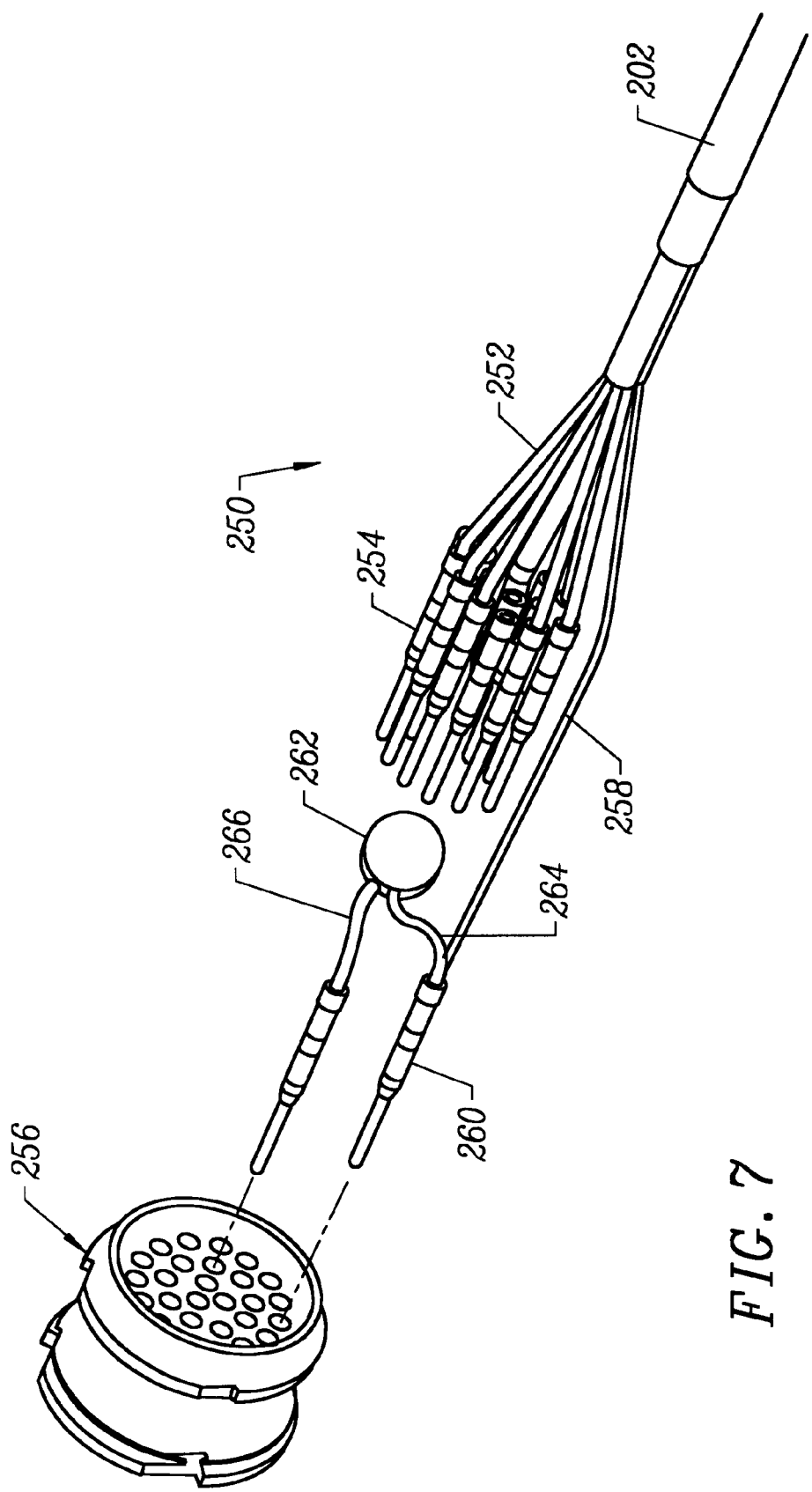
FIG. 7 is an exploded view of a proximal portion of the electrosurgical probe of FIG. 4.

FIG. 7 illustrates the electrical connections 250 within handle 204 for coupling electrode terminals 104 and return electrode 112 to the power supply 28. As shown, a plurality of wires 252 extend through shaft 100 to couple terminals 104 to a plurality of pins 254, which are plugged into a connector block 256 for coupling to a connecting cable 22 (FIG. 3). Similarly, return electrode 112 is coupled to connector block 256 via a wire 258 and a plug 260.

According to the present invention, the probe 90 further includes an identification element that is characteristic of the particular electrode assembly so that the same power supply 28 can be used for different electrosurgical operations. In one embodiment, for example, the probe 90 includes a voltage reduction element or a voltage reduction circuit for reducing the voltage applied between the electrode terminals 104 and the return electrode 112. The voltage reduction element serves to reduce the voltage applied by the power supply so that the voltage between the electrode terminals and the return electrode is low enough to avoid excessive power dissipation into the electrically conducting medium and/or ablation of the soft tissue at the target site. The voltage reduction element primarily allows the electrosurgical probe 90 to be compatible with other ArthroCare generators that are adapted to apply higher voltages for ablation or vaporization of tissue. For contraction of tissue, for example, the voltage reduction element will serve to reduce a voltage of about 100 to 135 volts rms (which is a setting of 1 on the ArthroCare Model 970 and 980 (i.e., 2000) Generators) to about 45 to 60 volts rms, which is a suitable voltage for contraction of tissue without ablation (e.g., molecular dissociation) of the tissue.

Of course, for some procedures, such as endoscopic sinus surgery, the probe will typically not require a voltage reduction element. Alternatively, the probe may include a voltage increasing element or circuit, if desired.

In the representative embodiment, the voltage reduction element is a dropping capacitor 262 which has first leg 264 coupled to the return electrode wire 258 and a second leg 266 coupled to connector block 256. Of course, the capacitor may be located in other places within the system, such as in, or distributed along the length of, the cable, the generator, the connector, etc. In addition, it will be recognized that other voltage reduction elements, such as diodes, transistors, inductors, resistors, capacitors or combinations thereof, may be used in conjunction with the present invention. For example, the probe 90 may include a coded resistor (not shown) that is constructed to lower the voltage applied between return electrode 112 and electrode terminals 104 to a suitable level for contraction of tissue. In addition, electrical circuits may be employed for this purpose.

Alternatively or additionally, the cable 22 that couples the power supply 10 to the probe 90 may be used as a voltage reduction element. The cable has an inherent capacitance that can be used to reduce the power supply voltage if the cable is placed into the electrical circuit between the power supply, the electrode terminals and the return electrode. In this embodiment, the cable 22 may be used alone, or in combination with one of the voltage reduction elements discussed above, e.g., a capacitor.

Further, it should be noted that the present invention can be used with a power supply that is adapted to apply a voltage within the selected range for treatment of tissue. In this embodiment, a voltage reduction element or circuitry may not be desired.

Figure 9:
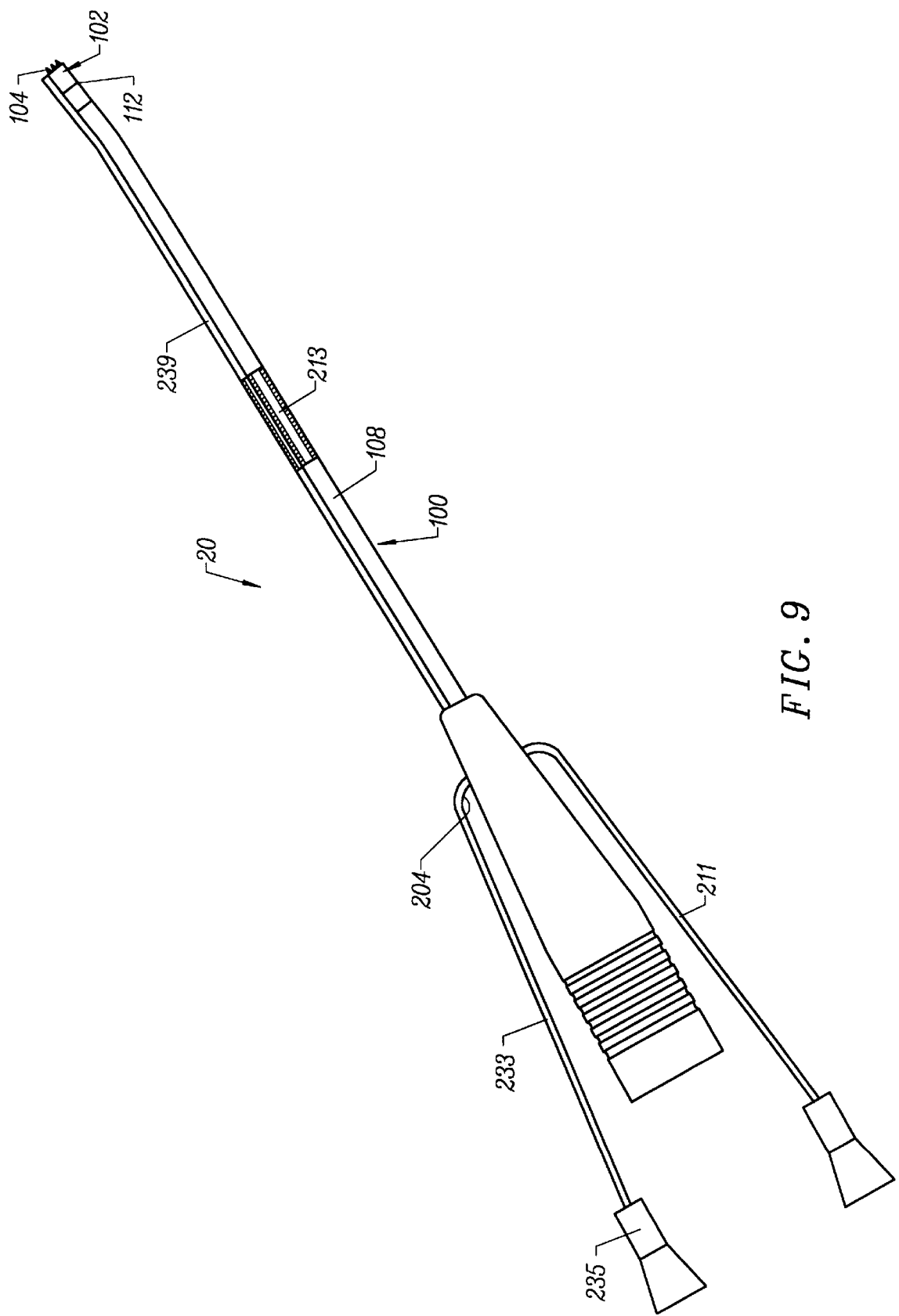
FIG. 9 is a side view of an electrosurgical probe designed for cutting tissue according to the present invention.
Figure 10:
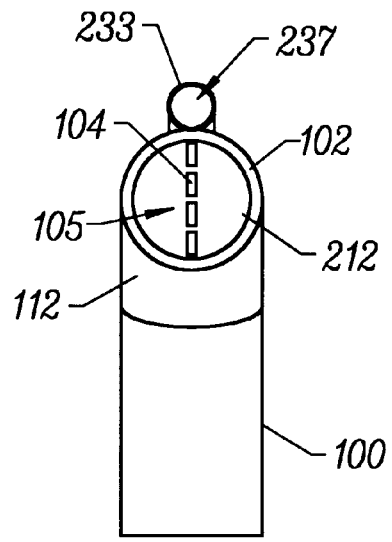
FIG. 10 is an end view of the probe of FIG. 9.
Figure 11:
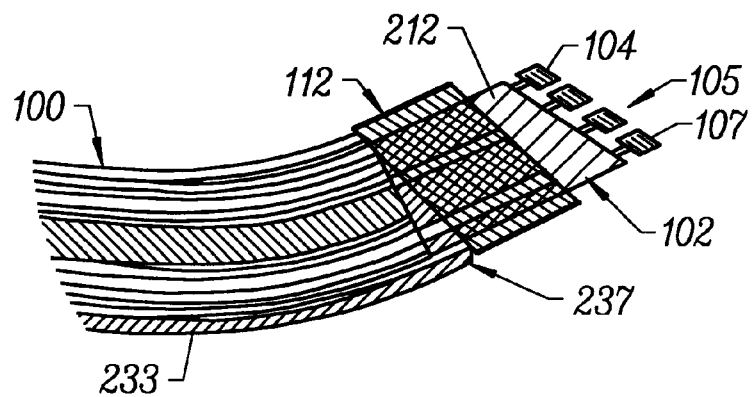
FIG. 11 is a cross sectional view of the electrosurgical probe of FIG. 9.

FIGS. 9–11 illustrate an electrosurgical probe 20 specifically designed for cutting tissue according to the present invention. As shown, probe 20 is similar to the probe described in FIGS. 4–7 except for a linear array 105 (FIG. 10) of electrode terminals 104 at its distal end. The electrically isolated electrode terminals 104 are preferably spaced from each other and aligned to form a linear array 105 for cutting a substantially linear incision in the tissue. The tissue treatment surface and individual electrode terminals 104 will usually have dimensions within the ranges set forth above. As shown in FIGS. 10 and 11, electrode terminals 104 preferably have a distal edge 107 to increase the electric field intensities around terminals 104, and to facilitate cutting of tissue. Thus, electrode terminals 104 have a screwdriver shape in the representative embodiment of FIGS. 9–11. In this embodiment, the tissue treatment surface 212 has a circular cross-sectional shape with a diameter in the range of about 1 mm to 30 mm, usually about 2 to 20 mm. The individual electrode terminals 104 preferably extend outward from tissue treatment surface 212 by a distance of about 0.1 to 8 mm, usually about 1 to 4 mm. Applicant has found that this configuration increases the high electric field intensities and associated current densities around electrode terminals 104 to facilitate the ablation of tissue as described in detail above.

Of course, the electrosurgical scalpel described above may have a variety of different configurations. A more complete description of some of these alternative configurations can be found in U.S. patent application No. 09/041, 934, filed Mar. 13, 1998 (Attorney Docket No. A-1-6), the complete disclosure of which is incorporated herein by reference.

Figure 12A:
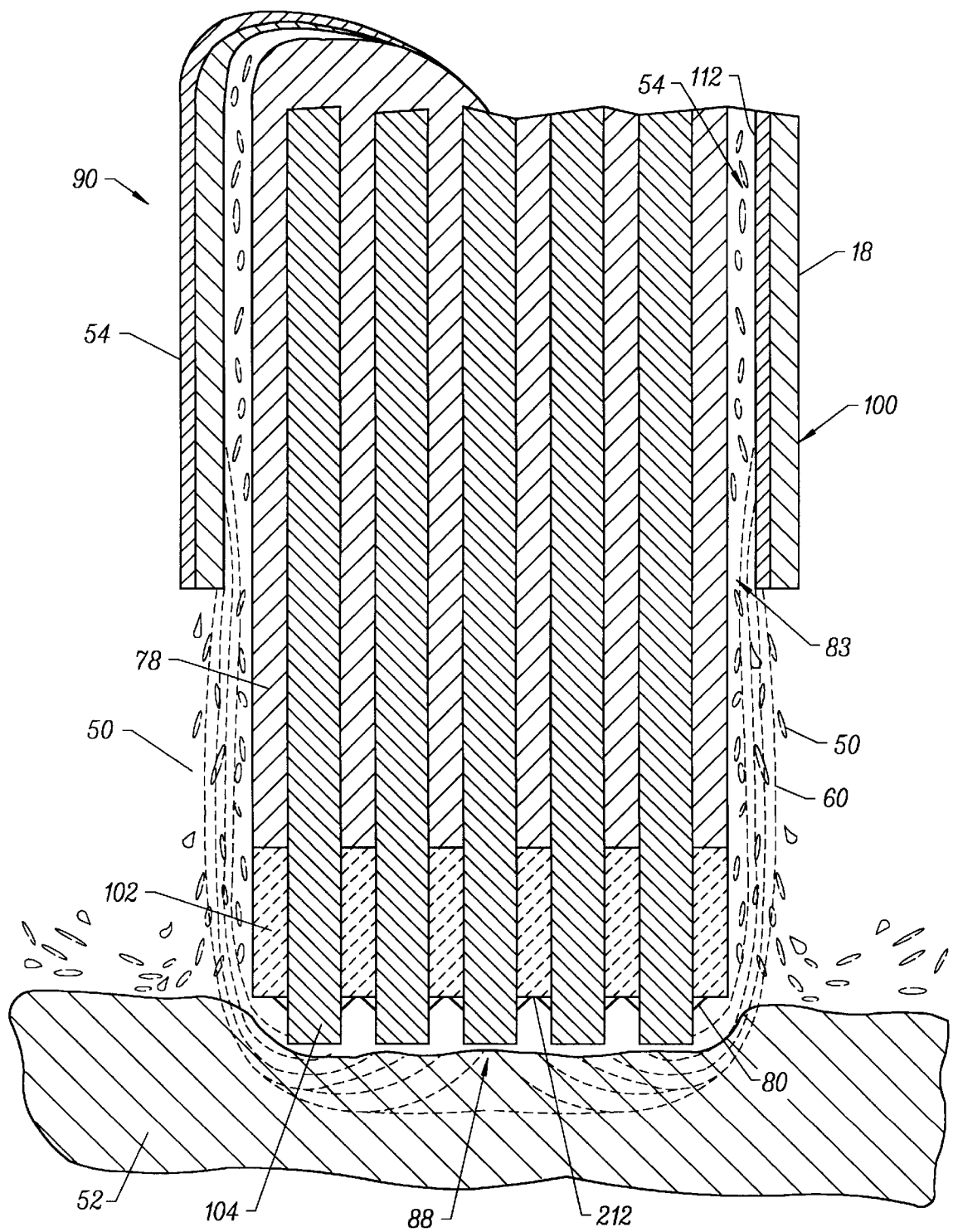
FIGS. 12A–12C are cross-sectional views of the distal portions of three different embodiments of an electrosurgical probe according to the present invention.
Figure 12B:
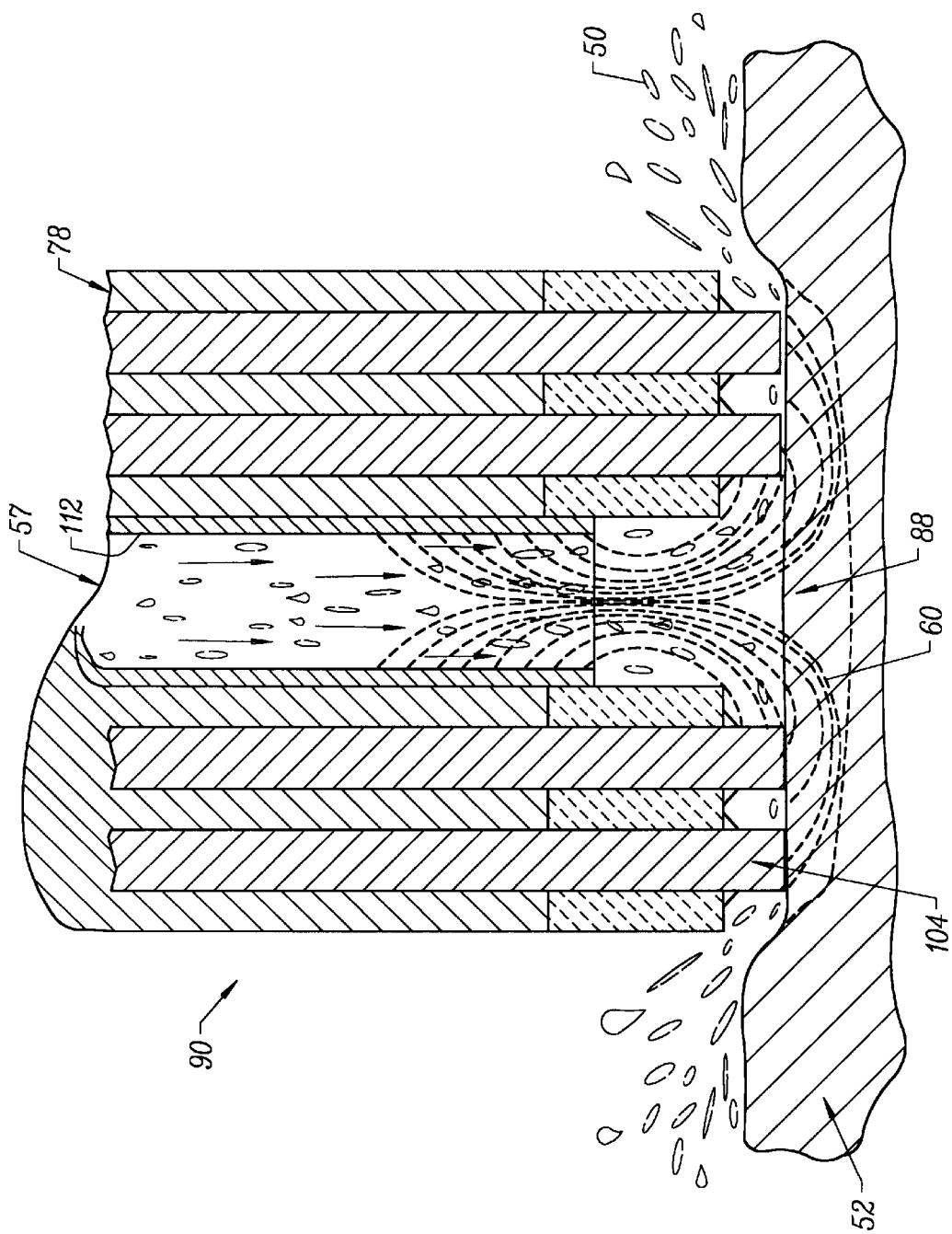
Figure 12C:
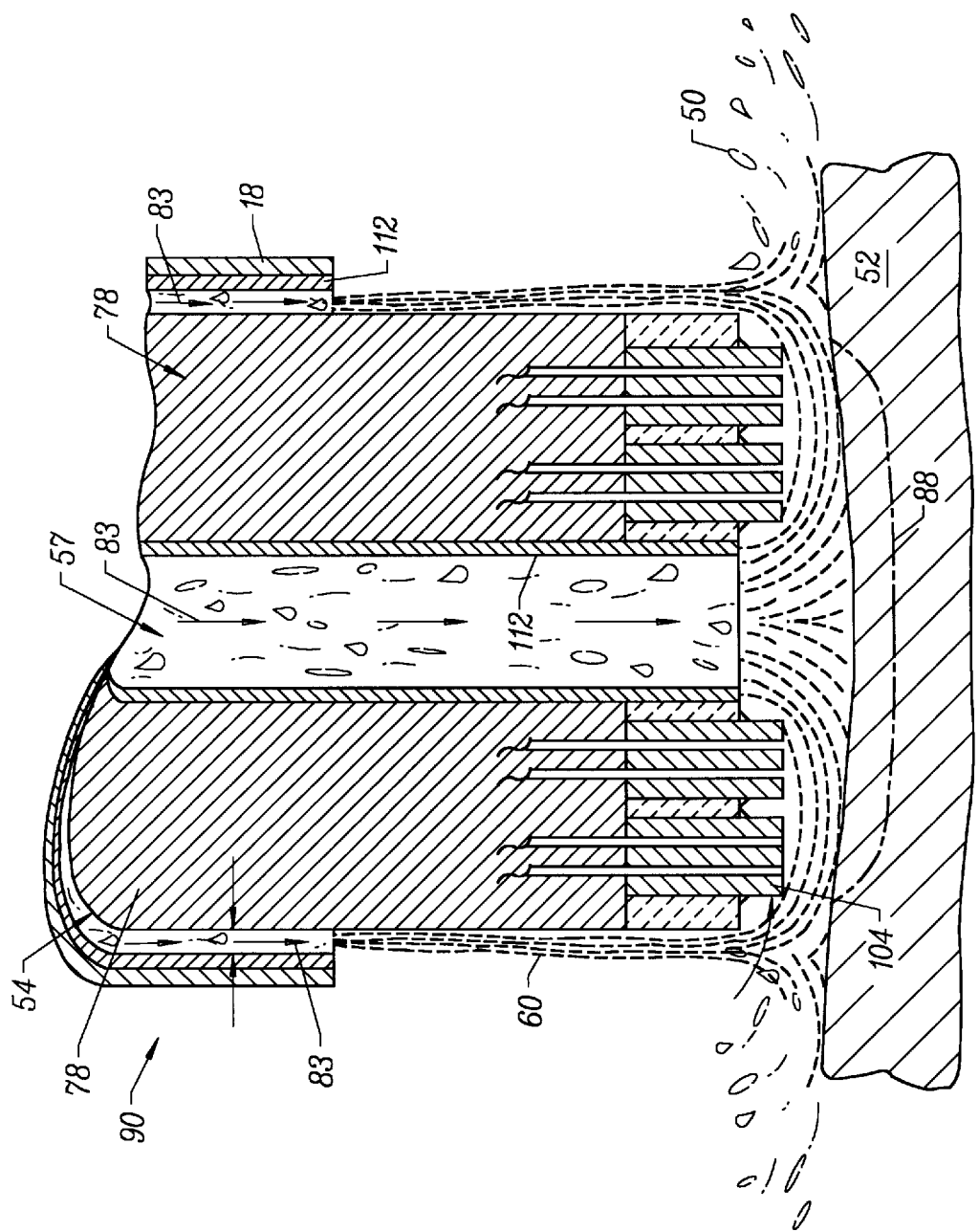

FIGS. 12A–12C schematically illustrate the distal portion of three different embodiments of probe 90 according to the present invention. As shown in FIG. 12A, electrode terminals 104 are anchored in a support marix 102 of suitable insulating material (e.g., ceramic or glass material, such as alumina, zirconia and the like) which could be formed at the time of manufacture in a flat, hemispherical or other shape according to the requirements of a particular procedure. The preferred support matrix material is alumina, available from Kyocera Industrial Ceramics Corporation, Elkgrove, Ill., because of its high thermal conductivity, good electrically insulative properties, high flexural modulus, resistance to carbon tracking, biocompatibility, and high melting point. The support matrix 102 is adhesively joined to a tubular support member 78 that extends most or all of the distance between matrix 102 and the proximal end of probe 90. Tubular member 78 preferably comprises an electrically insulating material, such as an epoxy or silicone-based material.

In a preferred construction technique, electrode terminals 104 extend through pre-formed openings in the support matrix 102 so that they protrude above tissue treatment surface 212 by the desired distance. The electrodes are then bonded to the tissue treatment surface 212 of support matrix 102, typically by an inorganic sealing material 80. Sealing material 80 is selected to provide effective electrical insulation, and good adhesion to both the alumina matrix 102 and the platinum or titanium electrode terminals. Sealing material 80 additionally should have a compatible thermal expansion coefficient and a melting point well below that of platinum or titanium and alumina or zirconia, typically being a glass or glass ceramic.

In the embodiment shown in FIG. 12A, return electrode 112 comprises an annular member positioned around the exterior of shaft 100 of probe 90. Return electrode 90 may fully or partially circumscribe tubular support member 78 to form an annular gap 54 therebetween for flow of electrically conducting liquid 50 therethrough, as discussed below. Gap 54 preferably has a width in the range of 0.25 mm to 4 mm. Alternatively, probe may include a plurality of longitudinal ribs between support member 78 and return electrode 112 to form a plurality of fluid lumens extending along the perimeter of shaft 100. In this embodiment, the plurality of lumens will extend to a plurality of openings.

Return electrode 112 is disposed within an electrically insulative jacket 18, which is typically formed as one or more electrically insulative sheaths or coatings, such as polytetrafluoroethylene, polyamide, and the like. The provision of the electrically insulative jacket 18 over return electrode 112 prevents direct electrical contact between return electrode 56 and any adjacent body structure. Such direct electrical contact between a body structure (e.g., tendon) and an exposed electrode member 112 could result in unwanted heating and necrosis of the structure at the point of contact causing necrosis.

As shown in FIG. 12A, return electrode 112 is not directly connected to electrode terminals 104. To complete this current path so that terminals 104 are electrically connected to return electrode 112, electrically conducting liquid 50 (e.g., isotonic saline) is caused to flow along fluid path(s) 83. Fluid path 83 is formed by annular gap 54 between outer return electrode 112 and tubular support member. The electrically conducting liquid 50 flowing through fluid path 83 provides a pathway for electrical current flow between electrode terminals 104 and return electrode 112, as illustrated by the current flux lines 60 in FIG. 12A. When a voltage difference is applied between electrode terminals 104 and return electrode 112, high electric field intensities will be generated at the distal tips of terminals 104 with current flow from terminals 104 through the target tissue to the return electrode, the high electric field intensities causing ablation of tissue 52 in zone 88.

FIG. 12B illustrates another alternative embodiment of electrosurgical probe 90 which has a return electrode 112 positioned within tubular member 78. Return electrode 112 is preferably a tubular member defining an inner lumen 57 for allowing electrically conducting liquid 50 (e.g., isotonic saline) to flow therethrough in electrical contact with return electrode 112. In this embodiment, a voltage difference is applied between electrode terminals 104 and return electrode 112 resulting in electrical current flow through the electrically conduct5 resuquid 50 as shown by current flux lines 60. As a result of the applied voltage difference and concomitant high electric field intensities at the tips of electrode terminals 104, tissue 52 becomes ablated or transected in zone 88.

FIG. 12C illustrates another embodiment of probe 90 that is a combination of the embodiments in FIGS. 12A and 12B. As shown, this probe includes both an inner lumen 57 and an outer gap or plurality of outer lumens 54 for flow of electrically conductive fluid. In this embodiment, the return electrode 112 may be positioned within tubular member 78 as in FIG. 12B, outside of tubular member 78 as in FIG. 12A, or in both locations.

Figure 15:
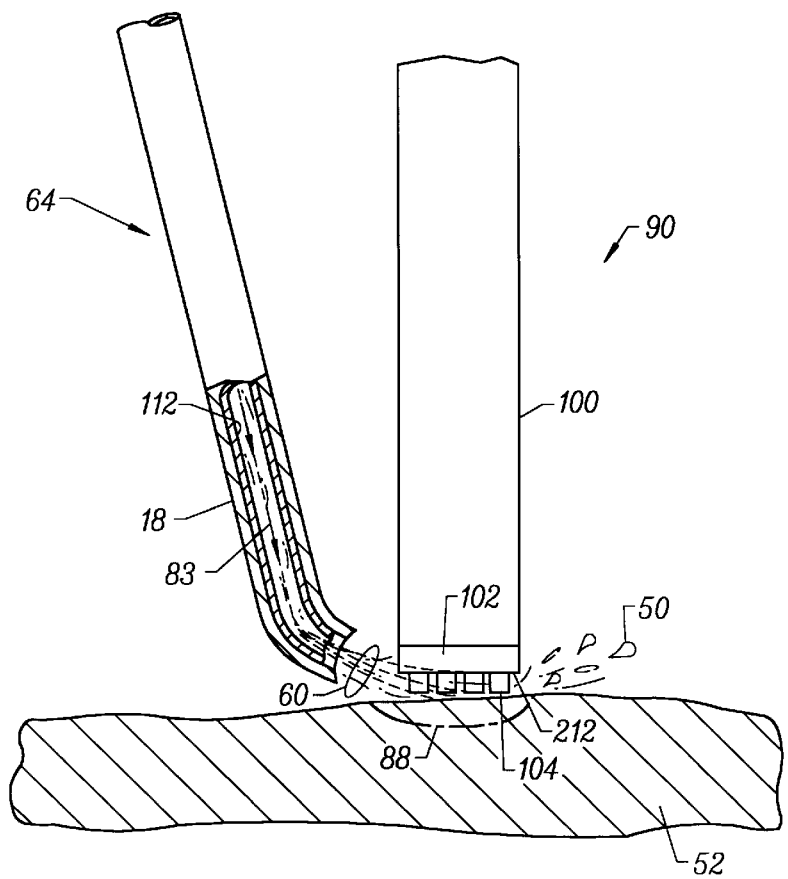
FIG. 15 illustrates an electrosurgical system with a separate fluid delivery instrument according to the present invention.

FIG. 15 illustrates another embodiment of probe 90 where the distal portion of shaft 100 is bent so that electrode terminals extend transversely to the shaft. Preferably, the distal portion of shaft 100 is perpendicular to the rest of the shaft so that tissue treatment surface 212 is generally parallel to the shaft axis. In this embodiment, return electrode 112 is mounted to the outer surface of shaft 100 and is covered with an electrically insulating jacket 18. The electrically conducting fluid 50 flows along flow path 83 through return electrode 112 and exits the distal end of electrode 112 at a point proximal of tissue treatment surface 212. The fluid is directed exterior of shaft to surface 212 to create a return current path from electrode terminals 104, through the fluid 50, to return electrode 12, as shown by current flux lines 60.

Figure 14:
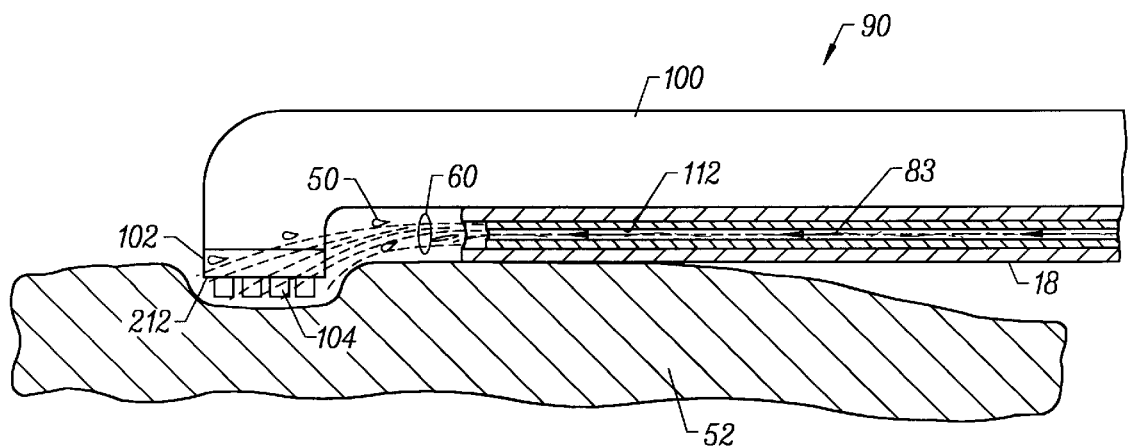
FIG. 14 illustrates an electrosurgical probe with a 90° distal bend and a lateral fluid lumen.

FIG. 14 illustrates another embodiment of the invention where electrosurgical system 11 further includes a liquid supply instrument 64 for supplying electrically conducting fluid 50 between electrode terminals 104 and return electrode 112. Liquid supply instrument 64 comprises an inner tubular member or return electrode 112 surrounded by an electrically insulating jacket 18. Return electrode 112 defines an inner passage 83 for flow of fluid 50. As shown in FIG. 14, the distal portion of instrument 64 is preferably bent so that liquid 50 is discharged at an angle with respect to instrument 64. This allows the surgical team to position liquid supply instrument 64 adjacent tissue treatment surface 212 with the proximal portion of supply instrument 64 oriented at a similar angle to probe 90.

Figure 13A:
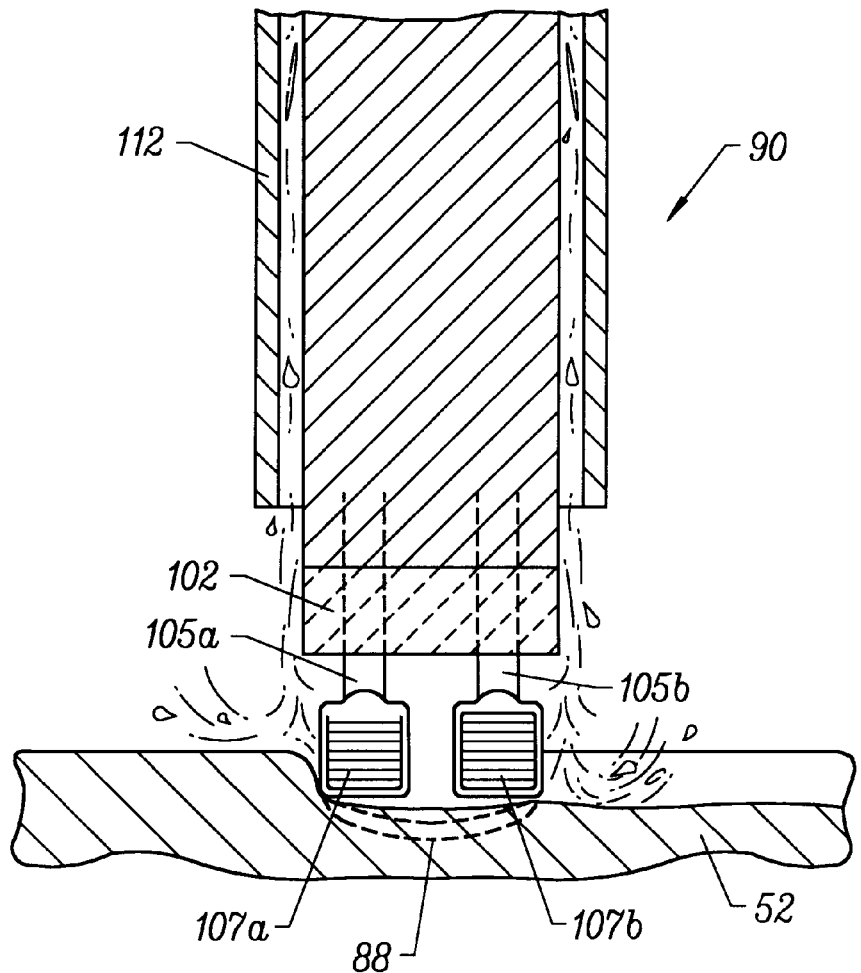
FIGS. 13A and 13B are cross-sectional and end views, respectively, of yet another electrosurgical probe incorporating flattened electrode terminals.
Figure 13B:
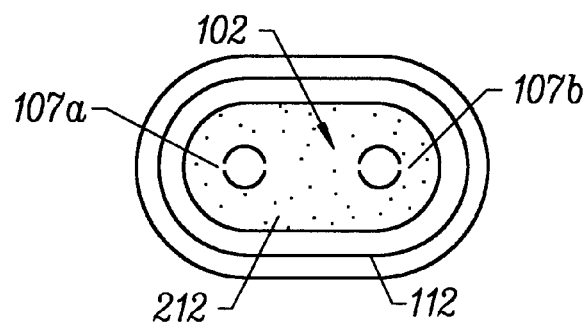

The present invention is not limited to an electrode array disposed on a relatively planar surface at the distal tip of probe 90, as described above. Referring to FIGS. 13A and 13B, an alternative probe 90 includes a pair of electrodes 105a, 105b mounted to the distal end of shaft 100. Electrodes 105a, 105b are electrically connected to power supply as described above and preferably have tips 107a, 107b with a screwdriver shape. The screwdriver shape provides a greater amount of "edges" to electrodes 105a,105b, to increase the electric field intensity and current density at the edges and thereby improve the cutting ability as well as the ability to limit bleeding from the incised tissue (i.e., hemostasis).

Figure 16:
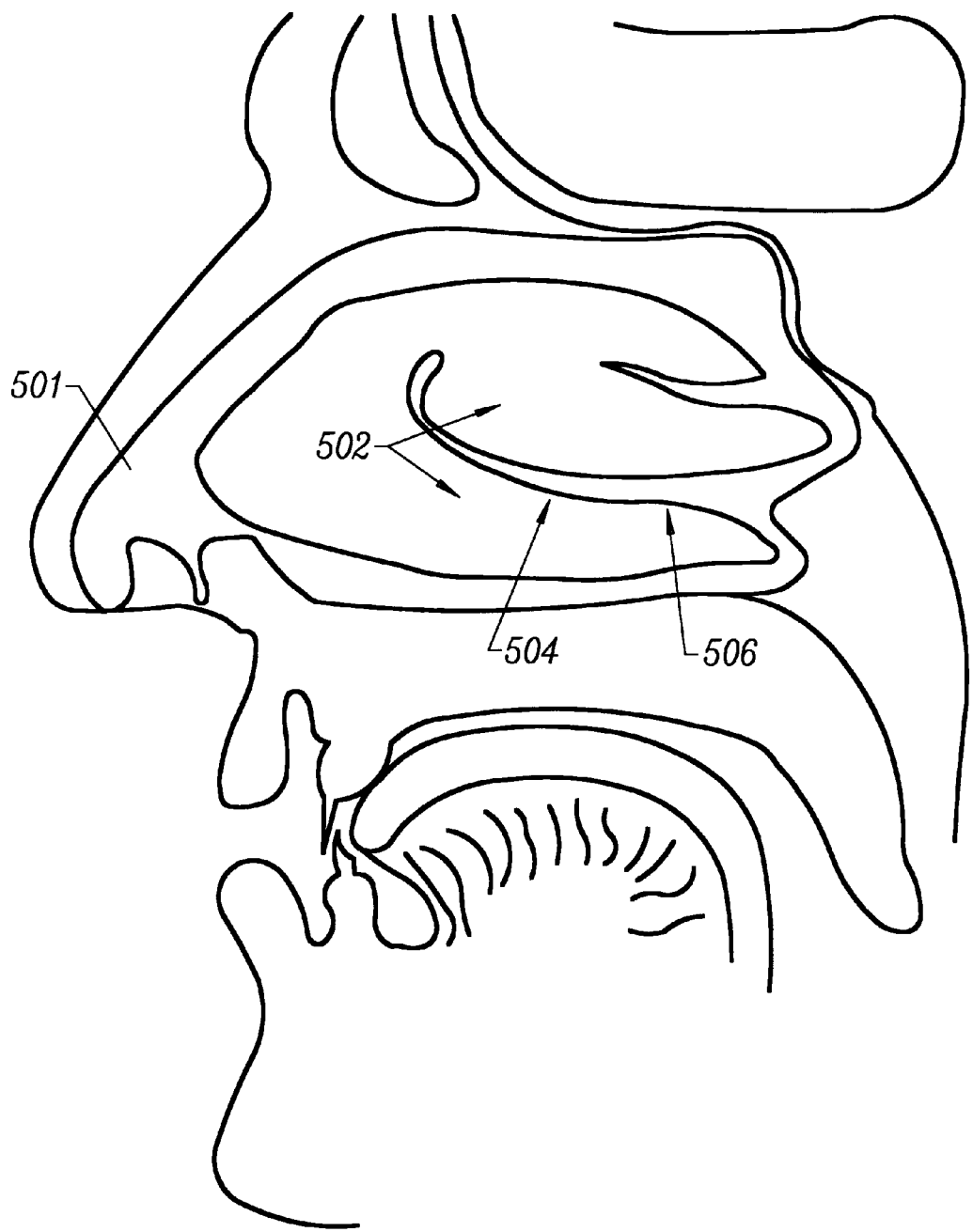
FIG. 16 illustrates a procedure for treating turbinates with the probe of FIG. 1.

FIGS. 16 and 17 illustrate a method for treating enlarged body structures, such as polyps or turbinates, according to the present invention. In these procedures., the polyps, turbinates or other sinus tissue may be ablated or reduced (e.g., by tissue contraction) to clear the blockage and/or prevent further swelling of the turbinates to reestablish normal sinus function. For example, in chronic rhinitis, which is a collective term for chronic irritation or inflammation of the nasal mucosa with hypertrophy of the nasal mucosa, the inferior turbinate may be reduced by ablation or contraction. Alternatively, a turbinectomy or mucotomy may be performed by removing a strip of tissue from the lower edge of the inferior turbinate to reduce the volume of the turbinate. For treating nasal polypi, which comprises benign pedicled or sessile masses of nasal or sinus mucosa caused by inflammation, the nasal polypi may be contracted or shrunk, or ablated by the method of the present invention. For treating severe sinusitis, a frontal sinus operation may be performed to introduce the electrosurgical probe to the site of blockage. The present invention may also be used to treat diseases of the septum, e.g., ablating or resecting portions of the septum for removal, straightening or reimplantation of the septum.

The present invention is particularly useful in reducing enlarged turbinates by volumetrically removing a portion of the turbinates. As shown in FIG. 16, a patient's nose 500 comprises a nasal cavity 501 having a set of turbinates 502, including a middle nasal concha 504 and an inferior nasal concha 506. The inferior nasal concha 506 generally comprises an anterior portion and a posterior portion. It has been found that ablating the inferior nasal concha 506, typically the anterior portion, does not substantially degrade its function. According to the present invention, the distal end of probe 10 (FIG. 1) is introduced through nasal passage 512 into the nasal cavity 501. The electrode terminals 58 are positioned adjacent the selected turbinate 506 and electrically conductive fluid is delivered through tube 110 and opening 209 to the tissue. The fluid flows past the return electrode 72 to the electrode terminals 58 at the distal end of the shaft. The rate of fluid flow is controlled with valve 17 (FIG. 3) such that the zone between the tissue and electrode support 70 is constantly immersed in the fluid. The power supply 28 is then turned on and adjusted such that a high frequency voltage difference is applied between electrode terminals 58 and return electrode 72. The electrically conductive fluid provides the conduction path between electrode terminals 58 and the return electrode 72. Once the probe 10 has been activated, the surgeon will positioned the electrode terminals in contact with, or close proximity to, the turbinate 506 to volumetrically remove turbinate tissue.

Figure 17A:
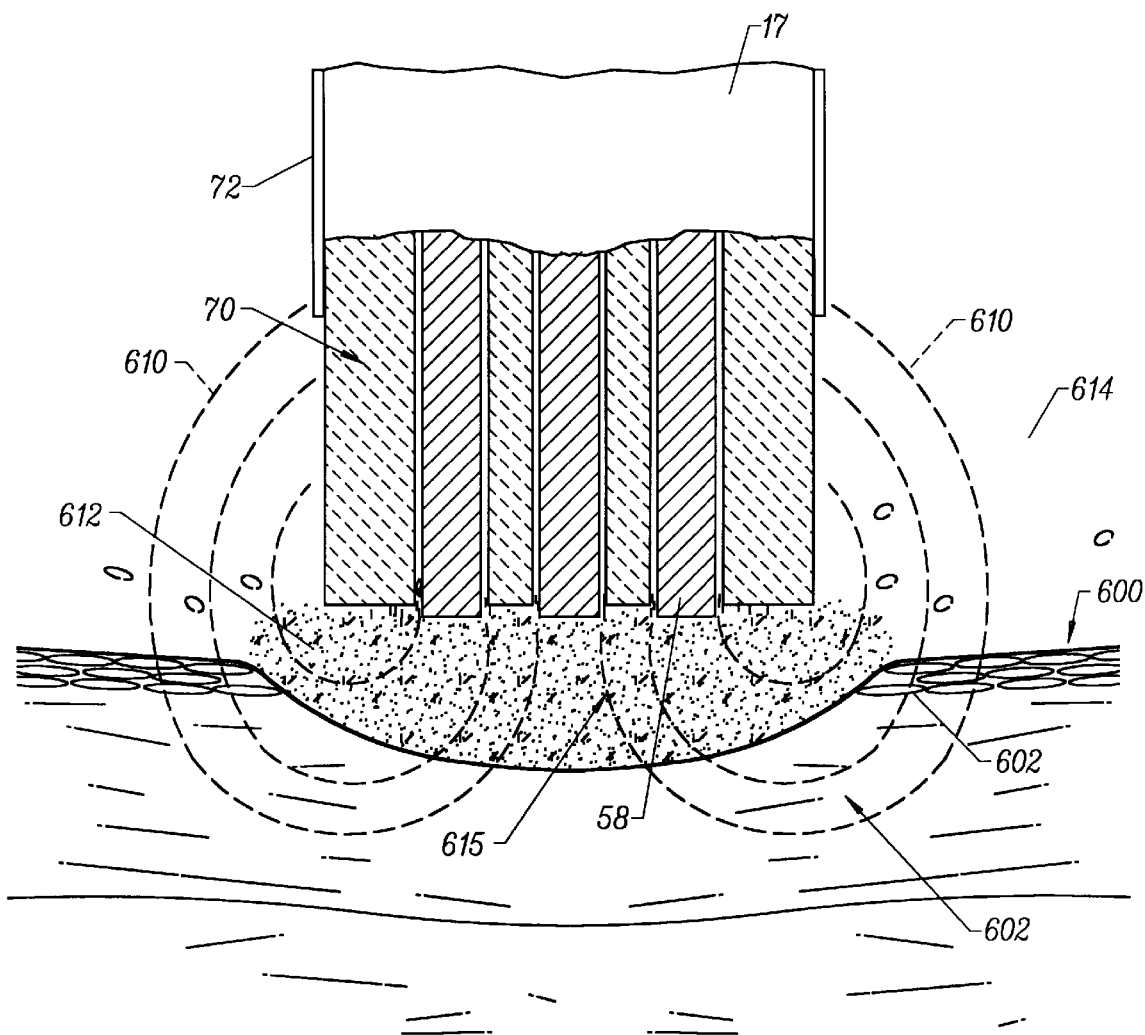
FIGS. 17A and 17B illustrate a detailed view of the turbinate procedure of FIG. 16, illustrating ablation of tissue according to the present invention.
Figure 17B:
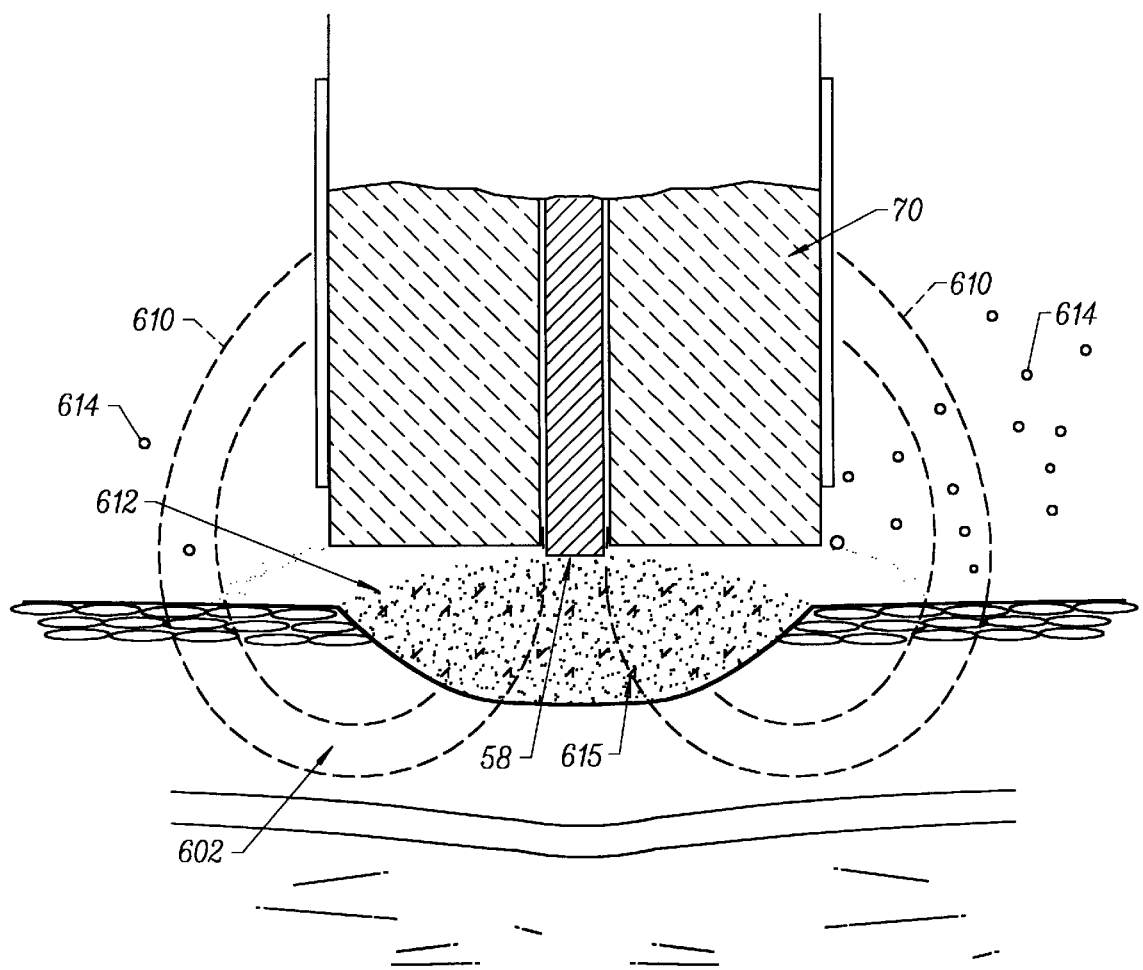

FIGS. 17A and 17B illustrate the removal of sinus tissue in more detail (FIG. 17B illustrates a single active electrode embodiment). As shown, a high frequency voltage difference is applied between electrode terminal(s) 58 and return electrode 72 such that electric current 610 flows through the conductive fluid to the high frequency voltage is sufficient to convert the electrically conductive fluid (not shown) between the target tissue 602 and electrode terminal(s) 58 into an ionized vapor layer 612 or plasma. As a result of the applied voltage difference between electrode terminal(s) 58 and the target tissue 602 (i.e., the voltage gradient across the plasma layer 612), charged particles 615 in the plasma (viz., electrons) are accelerated towards the tissue. At sufficiently high voltage differences, these charged particles 615 gain sufficient energy to cause dissociation of the molecular bonds within tissue structures. This molecular dissociation is accompanied by the volumetric removal (i.e, ablative sublimation) of tissue and the production of low molecular weight gases 614, such as oxygen, nitrogen, carbon dioxide, hydrogen and methane. The short range of the accelerated charged particles 615 within the tissue confines the molecular dissociation process to the surface layer to minimize damage and necrosis to the underlying tissue 620.

During the process, the gases 614 may be aspirated through a suction tube, instrument or lumen with shaft 17 (not shown) suitably coupled to a vacuum source. In addition, excess electrically conductive fluid, and other fluids (e.g., blood) may be aspirated from the target site to facilitate the surgeon's view. During ablation of the tissue, the residual heat generated by the current flux lines 610 (typically less than 150° C.), will usually be sufficient to coagulate any severed blood vessels at the site. If not, the surgeon may switch the power supply 28 into the coagulation mode by lowering the voltage to a level below the threshold for fluid vaporization, as discussed above. This simultaneous hemostasis results in less bleeding and facilitates the surgeon's ability to perform the procedure. Once the turbinate has been reduced, aeration and drainage are reestablished to allow the sinuses to heal and return to their normal function.

Depending on the procedure, the surgeon may translate the electrode terminals 58 relative to the turbinate tissue to form holes, channels, stripes, divots, craters or the like within the turbinate. In addition, the surgeon may purposely create some thermal damage within these holes, or channels to form scar tissue that will inhibit the turbinate from swelling after the procedure. In one embodiment, the physician axially translates the electrode terminals 58 into the turbinate tissue as the tissue is volumetrically removed to form one or more holes in the turbinate, typically having a diameter of less than 2 mm, preferably less than 1 mm. In another embodiment, the physician translates the electrode terminals 58 across the outer surface of the turbinates to form one or more channels or troughs. Applicant has found that the present invention can quickly and cleanly create such holes, divots or channels in tissue with the cold ablation technology described herein. A more complete description of methods for forming holes or channels in tissue can be found in U.S. Pat. No. 5,683,366, the complete disclosure of which is incorporated herein by reference for all purposes.

Another advantage of the present invention is the ability to precisely ablate channels or holes within the turbinates without causing necrosis or thermal damage to the underlying and surrounding tissues, nerves (e.g., the optic nerve) or bone. In addition, the voltage can be controlled so that the energy directed to the target site is insufficient to ablate bone or adipose tissue (which generally has a higher impedance than the target sinus tissue). In this manner, the surgeon can literally clean the tissue off the bone, without ablating or otherwise effecting significant damage to the bone.

What is claimed is:

1. A method for reducing the size of an enlarged turbinate within the patient's nose comprising:

positioning an electrode terminal adjacent to an enlarged turbinate:

applying high frequency voltage between the electrode terminal and a return electrode, the high frequency voltage being sufficient to volumetrically remove at least a portion of the turbinate; and during or after the applying step, advancing at least a distal end of the electrode terminal into a space vacated by the removed portion of the turbinate.

2. The method of claim 1 further comprising applying thermal energy to the turbinate to form a scar around the space.

3. The method of claim 1 further comprising axially translating the electrode terminal to form a hole through at least a portion of the turbinate.

4. The method of claim 3 wherein the hole has a diameter less than about 2 mm.

5. The method of claim 3 wherein the hole has a diameter less than about 1 mm.

6. The method of claim 1 further comprising transversely translating the electrode terminal relative to the turbinate to form a channel along the outer surface of the turbinate.

7. The method of claim 1 wherein the positioning step comprises:

introducing at least a distal end of an electrosurgical catheter into the patient's nose; and positioning the distal end of the catheter in close proximity to the turbinate.

8. The method of claim 1 wherein the positioning step comprises:

introducing at least a distal end of an electrosurgical probe through a nostril into the patient's nasal cavity; and positioning the distal end of the probe in close proximity to the turbinate.

positioning the distal end of the probe in close proximity to the turbinate.

9. The method of claim 1 further comprising an electrode array including a plurality of electrically isolated electrode terminals.

10. The method of claim 1 wherein the electrode terminal comprises a single electrode at or near a distal end of an electrosurgical probe.

11. The method of claim 1 wherein the return electrode is located on an external surface of the patient's body.

12. The method of claim 1 wherein the positioning step comprises introducing an electrosurgical probe into the patient's nose, wherein the return electrode and the electrode terminal are both located on the electrosurgical probe.

13. The method of claim 1 further comprising delivering electrically conductive fluid into the nose to substantially surround the electrode terminal with the electrically conductive fluid.

14. The method of claim 13 further comprising applying sufficient voltage to the electrode terminal in the presence of an electrically conducting fluid to vaporize at least a portion of the fluid between the electrode terminal and the turbinate.

15. The method of claim 14 further comprising accelerating charged particles from the vaporized fluid to the turbinate to cause dissociation of the molecular bonds within the turbinate.

16. The method of claim 1 further comprising delivering electrically conductive fluid into the nose to generate a current flow path between the return electrode and the electrode terminal.

17. The method of claim 1 further comprising aspirating fluid from a region around the turbinate during the removal step.

18. The method of claim 9 further comprising independently controlling current flow from at least two of the electrode terminals based on impedance between each electrode terminal and a return electrode.

* * * * *